(12) United States Patent
Eberhardt et al.

(10) Patent No.: US 9,331,328 B2
(45) Date of Patent: May 3, 2016

(54) PROSTHETIC CARDIAC VALVE FROM PERICARDIUM MATERIAL AND METHODS OF MAKING SAME

(75) Inventors: Carol Elsa Eberhardt, Fullerton, CA (US); Janice Lynn Shay, Lake Forest, CA (US)

(73) Assignee: Medtronic, Inc., Minneapolis, MN (US)

( * ) Notice: Subject to any disclaimer, the term of this patent is extended or adjusted under 35 U.S.C. 154(b) by 59 days.

(21) Appl. No.: 13/316,885

(22) Filed: Dec. 12, 2011

(65) Prior Publication Data
US 2012/0083879 A1 Apr. 5, 2012

Related U.S. Application Data

(63) Continuation of application No. 11/729,680, filed on Mar. 28, 2007, now Pat. No. 8,075,615.

(60) Provisional application No. 60/786,849, filed on Mar. 28, 2006.

(51) Int. Cl.
*A61F 2/24* (2006.01)
*H01M 4/131* (2010.01)
*H01M 4/485* (2010.01)
*H01M 4/58* (2010.01)
*H01M 10/0525* (2010.01)
*H01M 10/0565* (2010.01)
*H01M 10/0566* (2010.01)

(52) U.S. Cl.
CPC .............. *H01M 4/131* (2013.01); *H01M 4/485* (2013.01); *H01M 4/5825* (2013.01); *H01M 10/0525* (2013.01); *H01M 10/0565* (2013.01); *H01M 10/0566* (2013.01); *Y02E 60/122* (2013.01)

(58) Field of Classification Search
CPC ........................................................ A61F 2/24
USPC ........................................ 623/1.24, 2.1–2.17
See application file for complete search history.

(56) References Cited

U.S. PATENT DOCUMENTS

| | | | |
|---|---|---|---|
| 1,334,629 A | 8/1967 | Cohn | |
| 3,409,013 A | 11/1968 | Berry | |
| 3,540,431 A | 11/1970 | Mobin-Uddin | |
| 3,570,014 A | 3/1971 | Hancock | |
| 3,587,115 A | 6/1971 | Shiley | |

(Continued)

FOREIGN PATENT DOCUMENTS

| | | |
|---|---|---|
| CN | 2007-100074433 | 1/2007 |
| DE | 3640745 | 6/1987 |

(Continued)

*Primary Examiner* — Thomas J Sweet
*Assistant Examiner* — Seema Mathew

(57) ABSTRACT

A prosthetic stented heart valve which includes a compressible and expandable stent structure having first and second opposite ends, an expanded outer periphery, and a compressed outer periphery that is at least slightly smaller than the expanded outer periphery when subjected to an external radial force. The valve further includes a valve segment comprising a dual-layer sheet formed into a generally tubular shape having at least one longitudinally extending seam, and a plurality of leaflets formed by attachment of an outer layer of the dual-layer sheet to an inner layer of the dual-layer sheet in a leaflet defining pattern. The valve segment is at least partially positioned within the stent structure. The valve may further include at least one opening in the outer layer of the dual-layer sheet that is spaced from both the first and second ends of the stent structure.

21 Claims, 5 Drawing Sheets

(56) References Cited

U.S. PATENT DOCUMENTS

| | | | |
|---|---|---|---|
| 3,628,535 A | 12/1971 | Ostrowsky et al. |
| 3,642,004 A | 2/1972 | Osthagen et al. |
| 3,657,744 A | 4/1972 | Ersek |
| 3,671,979 A | 6/1972 | Moulopoulos |
| 3,714,671 A | 2/1973 | Edwards et al. |
| 3,736,598 A | 6/1973 | Bellhouse |
| 3,755,823 A | 9/1973 | Hancock |
| 3,795,246 A | 3/1974 | Sturgeon |
| 3,839,741 A | 10/1974 | Haller |
| 3,868,956 A | 3/1975 | Alfidi et al. |
| 3,874,388 A | 4/1975 | King et al. |
| 4,035,849 A | 7/1977 | Angell et al. |
| 4,056,854 A | 11/1977 | Boretos et al. |
| 4,106,129 A | 8/1978 | Carpentier et al. |
| 4,218,782 A | 8/1980 | Rygg |
| 4,222,126 A | 9/1980 | Boretos et al. |
| 4,233,690 A | 11/1980 | Akins |
| 4,259,753 A | 4/1981 | Liotta et al. |
| 4,265,694 A | 5/1981 | Boretos |
| 4,291,420 A | 9/1981 | Reul |
| 4,297,749 A | 11/1981 | Davis et al. |
| 4,339,831 A | 7/1982 | Johnson |
| 4,343,048 A | 8/1982 | Ross et al. |
| 4,345,340 A | 8/1982 | Rosen |
| 4,425,908 A | 1/1984 | Simon |
| 4,451,936 A | 6/1984 | Carpentier et al. |
| 4,470,157 A | 9/1984 | Love |
| 4,501,030 A | 2/1985 | Lane |
| 4,574,803 A | 3/1986 | Storz |
| 4,580,568 A | 4/1986 | Gianturco |
| 4,592,340 A | 6/1986 | Boyles |
| 4,610,688 A | 9/1986 | Silvestrini et al. |
| 4,612,011 A | 9/1986 | Kautzky |
| 4,624,822 A * | 11/1986 | Arru ................. A61F 2/2415 264/500 |
| 4,647,283 A | 3/1987 | Carpentier et al. |
| 4,648,881 A | 3/1987 | Carpentier et al. |
| 4,655,771 A | 4/1987 | Wallsten |
| 4,662,885 A | 5/1987 | DiPisa, Jr. |
| 4,665,906 A | 5/1987 | Jervis |
| 4,666,442 A | 5/1987 | Arru et al. |
| 4,681,908 A | 7/1987 | Broderick et al. |
| 4,687,483 A | 8/1987 | Fisher et al. |
| 4,692,164 A | 9/1987 | Dzemeshkevich et al. |
| 4,710,192 A | 12/1987 | Liotta et al. |
| 4,725,274 A | 2/1988 | Lane et al. |
| 4,733,665 A | 3/1988 | Palmaz |
| 4,777,951 A | 10/1988 | Cribier et al. |
| 4,787,899 A | 11/1988 | Lazarus |
| 4,790,843 A | 12/1988 | Carpentier et al. |
| 4,796,629 A | 1/1989 | Grayzel |
| 4,797,901 A | 1/1989 | Goerne et al. |
| 4,819,751 A | 4/1989 | Shimada et al. |
| 4,834,755 A | 5/1989 | Silvestrini et al. |
| 4,856,516 A | 8/1989 | Hillstead |
| 4,872,874 A | 10/1989 | Taheri |
| 4,878,495 A | 11/1989 | Grayzel |
| 4,878,906 A | 11/1989 | Lindemann et al. |
| 4,883,458 A | 11/1989 | Shiber |
| 4,909,252 A | 3/1990 | Goldberger |
| 4,917,102 A | 4/1990 | Miller et al. |
| 4,922,905 A | 5/1990 | Strecker |
| 4,954,126 A | 9/1990 | Wallsten |
| 4,966,604 A | 10/1990 | Reiss |
| 4,976,733 A | 12/1990 | Girardot |
| 4,979,939 A | 12/1990 | Shiber |
| 4,986,830 A | 1/1991 | Owens et al. |
| 4,994,077 A | 2/1991 | Dobben |
| 5,002,559 A | 3/1991 | Tower |
| 5,007,896 A | 4/1991 | Shiber |
| 5,026,366 A | 6/1991 | Leckrone |
| 5,032,128 A | 7/1991 | Alonso |
| 5,037,434 A * | 8/1991 | Lane ................. A61F 2/2418 623/2.18 |
| 5,047,041 A | 9/1991 | Samuels |
| 5,059,177 A | 10/1991 | Towne et al. |
| 5,061,273 A | 10/1991 | Yock |
| 5,061,277 A | 10/1991 | Carpentier et al. |
| 5,085,635 A | 2/1992 | Cragg |
| 5,089,015 A | 2/1992 | Ross |
| 5,147,391 A | 9/1992 | Lane |
| 5,152,771 A | 10/1992 | Sabbaghian et al. |
| 5,161,547 A | 11/1992 | Tower |
| 5,163,953 A | 11/1992 | Vince |
| 5,163,955 A | 11/1992 | Love et al. |
| 5,167,628 A | 12/1992 | Boyles |
| 5,217,483 A | 6/1993 | Tower |
| 5,232,445 A | 8/1993 | Bonzel |
| 5,258,023 A | 11/1993 | Reger |
| 5,272,909 A | 12/1993 | Nguyen et al. |
| 5,295,958 A | 3/1994 | Shturman |
| 5,327,774 A | 7/1994 | Nguyen et al. |
| 5,332,402 A | 7/1994 | Teitelbaum et al. |
| 5,350,398 A | 9/1994 | Pavcnik et al. |
| 5,370,685 A | 12/1994 | Stevens |
| 5,389,106 A | 2/1995 | Tower |
| 5,397,351 A | 3/1995 | Pavcnik et al. |
| 5,411,552 A | 5/1995 | Andersen et al. |
| 5,415,633 A | 5/1995 | Lazarus et al. |
| 5,431,676 A | 7/1995 | Dubrul et al. |
| 5,443,446 A | 8/1995 | Shturman |
| 5,469,868 A | 11/1995 | Reger |
| 5,480,424 A | 1/1996 | Cox |
| 5,489,294 A | 2/1996 | McVenes et al. |
| 5,489,297 A * | 2/1996 | Duran ................. A61F 2/2412 623/2.13 |
| 5,496,346 A | 3/1996 | Horzewski et al. |
| 5,500,014 A | 3/1996 | Quijano et al. |
| 5,507,767 A | 4/1996 | Maeda et al. |
| 5,509,930 A | 4/1996 | Love |
| 5,545,209 A | 8/1996 | Roberts et al. |
| 5,545,211 A | 8/1996 | An et al. |
| 5,545,214 A | 8/1996 | Stevens |
| 5,549,665 A | 8/1996 | Vesely et al. |
| 5,554,185 A | 9/1996 | Block et al. |
| 5,562,729 A | 10/1996 | Purdy et al. |
| 5,575,818 A | 11/1996 | Pinchuk |
| 5,580,922 A | 12/1996 | Park et al. |
| 5,591,195 A | 1/1997 | Taheri et al. |
| 5,609,626 A | 3/1997 | Quijano et al. |
| 5,645,559 A | 7/1997 | Hachtman et al. |
| 5,662,705 A | 9/1997 | Love et al. |
| 5,665,115 A | 9/1997 | Cragg |
| 5,667,523 A | 9/1997 | Bynon et al. |
| 5,674,277 A | 10/1997 | Freitag |
| 5,695,498 A | 12/1997 | Tower |
| 5,702,368 A | 12/1997 | Stevens et al. |
| 5,713,953 A * | 2/1998 | Vallana ................. A61F 2/2412 623/2.15 |
| 5,716,417 A | 2/1998 | Girard et al. |
| 5,746,709 A | 5/1998 | Rom et al. |
| 5,749,890 A | 5/1998 | Shaknovich |
| 5,766,151 A | 6/1998 | Valley et al. |
| 5,782,809 A | 7/1998 | Umeno et al. |
| 5,800,456 A | 9/1998 | Maeda et al. |
| 5,800,508 A | 9/1998 | Goicoechea et al. |
| 5,817,126 A | 10/1998 | Imran |
| 5,824,041 A | 10/1998 | Lenker |
| 5,824,043 A | 10/1998 | Cottone, Jr. |
| 5,824,053 A | 10/1998 | Khosravi et al. |
| 5,824,056 A | 10/1998 | Rosenberg |
| 5,824,061 A | 10/1998 | Quijano et al. |
| 5,824,064 A | 10/1998 | Taheri |
| 5,840,081 A | 11/1998 | Andersen et al. |
| 5,843,158 A | 12/1998 | Lenker et al. |
| 5,851,232 A | 12/1998 | Lois |
| 5,855,597 A | 1/1999 | Jayaraman |
| 5,855,601 A | 1/1999 | Bessler et al. |
| 5,860,966 A | 1/1999 | Tower |
| 5,861,028 A | 1/1999 | Angell |
| 5,868,783 A | 2/1999 | Tower |
| 5,876,448 A | 3/1999 | Thompson et al. |
| 5,888,201 A | 3/1999 | Stinson et al. |
| 5,891,191 A | 4/1999 | Stinson |

(56) References Cited

U.S. PATENT DOCUMENTS

| | | |
|---|---|---|
| 5,906,619 A | 5/1999 | Olson et al. |
| 5,907,893 A | 6/1999 | Zadno-Azizi et al. |
| 5,910,170 A | 6/1999 | Reimink et al. |
| 5,913,842 A | 6/1999 | Boyd et al. |
| 5,925,063 A | 7/1999 | Khosravi |
| 5,928,281 A | 7/1999 | Huynh et al. |
| 5,944,738 A | 8/1999 | Amplatz et al. |
| 5,954,766 A | 9/1999 | Zadno-Azizi et al. |
| 5,957,949 A | 9/1999 | Leonhardt et al. |
| 5,961,549 A | 10/1999 | Nguyen et al. |
| 5,968,068 A | 10/1999 | Dehdashtian et al. |
| 5,984,957 A | 11/1999 | Laptewicz, Jr. et al. |
| 5,984,959 A | 11/1999 | Robertson et al. |
| 5,997,573 A | 12/1999 | Quijano et al. |
| 6,022,370 A | 2/2000 | Tower |
| 6,027,525 A | 2/2000 | Suh et al. |
| 6,029,671 A | 2/2000 | Stevens et al. |
| 6,042,589 A | 3/2000 | Marianne |
| 6,042,598 A | 3/2000 | Tsugita et al. |
| 6,042,607 A | 3/2000 | Williamson, IV |
| 6,051,014 A | 4/2000 | Jang |
| 6,059,809 A | 5/2000 | Amor et al. |
| 6,059,827 A | 5/2000 | Fenton, Jr. |
| 6,110,201 A | 8/2000 | Quijano et al. |
| 6,146,366 A | 11/2000 | Schachar |
| 6,159,239 A | 12/2000 | Greenhalgh |
| 6,162,208 A | 12/2000 | Hipps |
| 6,162,245 A | 12/2000 | Jayaraman |
| 6,168,614 B1 | 1/2001 | Andersen et al. |
| 6,171,335 B1 | 1/2001 | Wheatley et al. |
| 6,200,336 B1 | 3/2001 | Pavcnik et al. |
| 6,203,550 B1 | 3/2001 | Olson |
| 6,210,408 B1 | 4/2001 | Chandrasekaran et al. |
| 6,218,662 B1 | 4/2001 | Tchakarov et al. |
| 6,221,006 B1 | 4/2001 | Dubrul et al. |
| 6,221,091 B1 | 4/2001 | Khosravi |
| 6,241,757 B1 | 6/2001 | An et al. |
| 6,245,102 B1 | 6/2001 | Jayaraman |
| 6,248,116 B1 | 6/2001 | Chevilon |
| 6,254,636 B1 | 7/2001 | Peredo |
| 6,258,114 B1 | 7/2001 | Konya et al. |
| 6,258,115 B1 | 7/2001 | Dubrul |
| 6,258,120 B1 | 7/2001 | McKenzie et al. |
| 6,277,555 B1 | 8/2001 | Duran et al. |
| 6,287,334 B1 * | 9/2001 | Moll ............... A61F 2/2412 128/898 |
| 6,299,637 B1 | 10/2001 | Shaolia et al. |
| 6,302,906 B1 | 10/2001 | Goicoechea et al. |
| 6,309,382 B1 | 10/2001 | Garrison et al. |
| 6,309,417 B1 | 10/2001 | Spence et al. |
| 6,327,772 B1 | 12/2001 | Zadno-Azizi et al. |
| 6,334,873 B1 | 1/2002 | Lane et al. |
| 6,338,735 B1 | 1/2002 | Stevens |
| 6,348,063 B1 | 2/2002 | Yassour et al. |
| 6,350,277 B1 | 2/2002 | Kocur |
| 6,352,708 B1 | 3/2002 | Duran et al. |
| 6,371,970 B1 | 4/2002 | Khosravi et al. |
| 6,371,983 B1 | 4/2002 | Lane |
| 6,375,679 B1 * | 4/2002 | Martyn ............. A61F 2/2412 623/2.12 |
| 6,379,383 B1 | 4/2002 | Palmaz et al. |
| 6,380,457 B1 | 4/2002 | Yurek et al. |
| 6,398,807 B1 | 6/2002 | Chouinard et al. |
| 6,409,750 B1 | 6/2002 | Hyodoh et al. |
| 6,425,916 B1 | 7/2002 | Garrison et al. |
| 6,440,164 B1 | 8/2002 | DiMatteo et al. |
| 6,454,798 B1 * | 9/2002 | Moe ............... A61F 2/2412 623/2.12 |
| 6,454,799 B1 | 9/2002 | Schreck |
| 6,458,153 B1 | 10/2002 | Bailey et al. |
| 6,461,382 B1 | 10/2002 | Cao |
| 6,468,303 B1 | 10/2002 | Amplatz et al. |
| 6,468,305 B1 | 10/2002 | Otte |
| 6,475,239 B1 | 11/2002 | Campbell et al. |
| 6,482,228 B1 | 11/2002 | Norred |
| 6,488,704 B1 | 12/2002 | Connelly et al. |
| 6,491,511 B1 * | 12/2002 | Duran ............... A61F 2/2415 425/394 |
| 6,494,909 B2 | 12/2002 | Greenhalgh |
| 6,503,272 B2 | 1/2003 | Duerig et al. |
| 6,508,833 B2 | 1/2003 | Pavcnik et al. |
| 6,527,800 B1 | 3/2003 | McGuckin, Jr. et al. |
| 6,530,949 B2 | 3/2003 | Konya et al. |
| 6,530,952 B2 | 3/2003 | Vesely |
| 6,544,285 B1 * | 4/2003 | Thubrikar ......... A61F 2/2412 623/2.12 |
| 6,562,031 B2 | 5/2003 | Chandrasekaran et al. |
| 6,562,058 B2 | 5/2003 | Seguin et al. |
| 6,569,196 B1 | 5/2003 | Vesely |
| 6,585,758 B1 | 7/2003 | Chouinard et al. |
| 6,592,546 B1 | 7/2003 | Barbut et al. |
| 6,605,112 B1 | 8/2003 | Moll et al. |
| 6,613,077 B2 | 9/2003 | Gilligan et al. |
| 6,622,604 B1 | 9/2003 | Chouinard et al. |
| 6,632,243 B1 | 10/2003 | Zadno-Azizi et al. |
| 6,635,068 B1 | 10/2003 | Dubrul et al. |
| 6,652,571 B1 | 11/2003 | White et al. |
| 6,652,578 B2 | 11/2003 | Bailey et al. |
| 6,656,213 B2 | 12/2003 | Solem |
| 6,663,663 B2 | 12/2003 | Kim et al. |
| 6,669,724 B2 | 12/2003 | Park et al. |
| 6,673,089 B1 | 1/2004 | Yassour et al. |
| 6,673,109 B2 | 1/2004 | Cox |
| 6,676,698 B2 | 1/2004 | McGuckin, Jr. et al. |
| 6,682,558 B2 | 1/2004 | Tu et al. |
| 6,682,559 B2 | 1/2004 | Myers et al. |
| 6,685,739 B2 | 2/2004 | DiMatteo et al. |
| 6,689,144 B2 | 2/2004 | Gerberding |
| 6,689,164 B1 | 2/2004 | Seguin |
| 6,692,512 B2 | 2/2004 | Jang |
| 6,692,513 B2 | 2/2004 | Streeter et al. |
| 6,695,878 B2 | 2/2004 | McGuckin, Jr. et al. |
| 6,702,851 B1 | 3/2004 | Chinn et al. |
| 6,709,457 B1 | 3/2004 | Otte et al. |
| 6,716,244 B2 | 4/2004 | Klaco |
| 6,719,789 B2 | 4/2004 | Cox |
| 6,730,118 B2 | 5/2004 | Spenser et al. |
| 6,730,377 B2 | 5/2004 | Wang |
| 6,733,525 B2 | 5/2004 | Yang et al. |
| 6,736,846 B2 | 5/2004 | Cox |
| 6,752,828 B2 | 6/2004 | Thornton |
| 6,758,855 B2 | 7/2004 | Fulton, III et al. |
| 6,769,434 B2 | 8/2004 | Liddicoat et al. |
| 6,786,925 B1 | 9/2004 | Schoon |
| 6,790,229 B1 | 9/2004 | Berreklouw |
| 6,792,979 B2 | 9/2004 | Konya et al. |
| 6,797,000 B2 | 9/2004 | Simpson et al. |
| 6,797,002 B2 | 9/2004 | Spence |
| 6,821,297 B2 | 11/2004 | Snyders |
| 6,830,575 B2 | 12/2004 | Stenzel et al. |
| 6,830,584 B1 | 12/2004 | Seguin |
| 6,830,585 B1 | 12/2004 | Artof |
| 6,846,325 B2 | 1/2005 | Liddicoat |
| 6,866,650 B2 | 3/2005 | Stevens |
| 6,872,223 B2 | 3/2005 | Roberts |
| 6,872,226 B2 | 3/2005 | Cali et al. |
| 6,875,231 B2 | 4/2005 | Anduiza et al. |
| 6,883,522 B2 | 4/2005 | Spence et al. |
| 6,887,266 B2 | 5/2005 | Williams et al. |
| 6,890,330 B2 | 5/2005 | Streeter et al. |
| 6,893,460 B2 | 5/2005 | Spenser et al. |
| 6,896,690 B1 | 5/2005 | Lambrecht et al. |
| 6,908,481 B2 | 6/2005 | Cribier |
| 6,913,600 B2 | 7/2005 | Valley et al. |
| 6,929,653 B2 | 8/2005 | Streeter |
| 6,936,066 B2 | 8/2005 | Palmaz et al. |
| 6,939,365 B1 | 9/2005 | Fogarty et al. |
| 6,951,571 B1 | 10/2005 | Srivastava |
| 6,986,742 B2 | 1/2006 | Hart et al. |
| 6,989,027 B2 | 1/2006 | Allen et al. |
| 6,989,028 B2 | 1/2006 | Lashinski et al. |
| 6,991,649 B2 | 1/2006 | Sievers |
| 7,018,401 B1 | 3/2006 | Hyodoh et al. |
| 7,041,128 B2 | 5/2006 | McGuckin, Jr. et al. |

(56) References Cited

U.S. PATENT DOCUMENTS

| | | |
|---|---|---|
| 7,044,966 B2 | 5/2006 | Svanidze et al. |
| 7,048,014 B2 | 5/2006 | Hyodoh et al. |
| 7,097,659 B2 | 8/2006 | Woolfson et al. |
| 7,101,396 B2 | 9/2006 | Artof et al. |
| 7,105,016 B2 | 9/2006 | Shui et al. |
| 7,115,141 B2 | 10/2006 | Menz et al. |
| 7,141,064 B2 | 11/2006 | Scott et al. |
| 7,147,663 B1 | 12/2006 | Berg et al. |
| 7,153,324 B2 | 12/2006 | Case et al. |
| 7,160,319 B2 | 1/2007 | Chouinard et al. |
| 7,175,656 B2 | 2/2007 | Khairkhahan |
| 7,186,265 B2 | 3/2007 | Sharkawy et al. |
| 7,195,641 B2 | 3/2007 | Palmaz et al. |
| 7,198,646 B2 | 4/2007 | Figulla et al. |
| 7,201,761 B2 | 4/2007 | Woolfson et al. |
| 7,201,772 B2 | 4/2007 | Schwammenthal et al. |
| 7,238,200 B2 | 7/2007 | Lee et al. |
| 7,252,682 B2 | 8/2007 | Seguin |
| 7,300,457 B2 | 11/2007 | Palmaz |
| 7,300,463 B2 | 11/2007 | Liddicoat |
| 7,316,706 B2 | 1/2008 | Bloom et al. |
| 7,329,278 B2 | 2/2008 | Seguin |
| 7,335,218 B2 | 2/2008 | Wilson et al. |
| 7,338,520 B2 | 3/2008 | Bailey et al. |
| 7,374,571 B2 | 5/2008 | Pease et al. |
| 7,381,218 B2 | 6/2008 | Shreck |
| 7,384,411 B1 | 6/2008 | Condado |
| 7,429,269 B2 | 9/2008 | Schwammenthal et al. |
| 7,442,204 B2 | 10/2008 | Schwammenthal et al. |
| 7,462,191 B2 | 12/2008 | Spenser et al. |
| 7,470,284 B2 | 12/2008 | Lambrecht et al. |
| 7,481,838 B2 | 1/2009 | Carpentier et al. |
| 7,544,206 B2 | 6/2009 | Cohn et al. |
| 7,556,646 B2 | 7/2009 | Yang et al. |
| 8,075,615 B2 * | 12/2011 | Eberhardt ............ A61F 2/2415 623/2.15 |
| 8,312,825 B2 * | 11/2012 | Holecek ............... A61F 2/2415 112/470.14 |
| 8,506,620 B2 * | 8/2013 | Ryan .................... A61F 2/2418 623/1.24 |
| 8,512,397 B2 * | 8/2013 | Rolando ...................... 623/1.26 |
| 8,696,743 B2 * | 4/2014 | Holecek ............... A61F 2/2412 623/1.24 |
| 2001/0001314 A1 | 5/2001 | Davison et al. |
| 2001/0002445 A1 | 5/2001 | Vesely |
| 2001/0007956 A1 | 7/2001 | Letac et al. |
| 2001/0010017 A1 | 7/2001 | Letac et al. |
| 2001/0011189 A1 | 8/2001 | Drasler et al. |
| 2001/0021872 A1 | 9/2001 | Bailey et al. |
| 2001/0025196 A1 | 9/2001 | Chinn et al. |
| 2001/0032013 A1 | 10/2001 | Marton |
| 2001/0039450 A1 | 11/2001 | Pavcnik et al. |
| 2001/0041928 A1 | 11/2001 | Pavcnik et al. |
| 2001/0044647 A1 | 11/2001 | Pinchuk et al. |
| 2002/0010508 A1 | 1/2002 | Chobotov |
| 2002/0026238 A1 | 2/2002 | Lane et al. |
| 2002/0029014 A1 | 3/2002 | Jayaraman |
| 2002/0032480 A1 | 3/2002 | Spence et al. |
| 2002/0032481 A1 | 3/2002 | Gabbay |
| 2002/0035396 A1 | 3/2002 | Heath |
| 2002/0042650 A1 | 4/2002 | Vardi et al. |
| 2002/0052651 A1 | 5/2002 | Myers et al. |
| 2002/0058995 A1 | 5/2002 | Stevens |
| 2002/0072789 A1 | 6/2002 | Hackett et al. |
| 2002/0077696 A1 | 6/2002 | Zadno-Azizi et al. |
| 2002/0095209 A1 | 7/2002 | Zadno-Azizi et al. |
| 2002/0099439 A1 | 7/2002 | Schwartz et al. |
| 2002/0103533 A1 | 8/2002 | Langberg et al. |
| 2002/0107565 A1 | 8/2002 | Greenhalgh |
| 2002/0111674 A1 | 8/2002 | Chouinard et al. |
| 2002/0116053 A1 | 8/2002 | Simpson et al. |
| 2002/0123802 A1 | 9/2002 | Snyders |
| 2002/0133183 A1 | 9/2002 | Lentz et al. |
| 2002/0138138 A1 | 9/2002 | Yang |
| 2002/0151970 A1 | 10/2002 | Garrison et al. |
| 2002/0161392 A1 | 10/2002 | Dubrul |
| 2002/0161394 A1 | 10/2002 | Macoviak et al. |
| 2002/0193871 A1 | 12/2002 | Beyersdorf et al. |
| 2003/0014104 A1 | 1/2003 | Cribier |
| 2003/0023300 A1 | 1/2003 | Bailey et al. |
| 2003/0023302 A1 | 1/2003 | Moe et al. |
| 2003/0023303 A1 | 1/2003 | Palmaz et al. |
| 2003/0028247 A1 | 2/2003 | Cali |
| 2003/0036791 A1 | 2/2003 | Philipp et al. |
| 2003/0040771 A1 | 2/2003 | Hyodoh et al. |
| 2003/0040772 A1 | 2/2003 | Hyodoh et al. |
| 2003/0040792 A1 | 2/2003 | Gabbay |
| 2003/0050694 A1 | 3/2003 | Yang et al. |
| 2003/0055495 A1 | 3/2003 | Pease et al. |
| 2003/0065386 A1 | 4/2003 | Weadock |
| 2003/0069492 A1 | 4/2003 | Abrams et al. |
| 2003/0109924 A1 | 6/2003 | Cribier |
| 2003/0125795 A1 | 7/2003 | Pavcnik et al. |
| 2003/0130726 A1 | 7/2003 | Thorpe et al. |
| 2003/0130729 A1 | 7/2003 | Paniagua et al. |
| 2003/0139804 A1 | 7/2003 | Hankh et al. |
| 2003/0139805 A1 | 7/2003 | Holmberg et al. |
| 2003/0149475 A1 | 8/2003 | Hyodoh et al. |
| 2003/0149476 A1 | 8/2003 | Damm et al. |
| 2003/0149478 A1 | 8/2003 | Figulla et al. |
| 2003/0153974 A1 | 8/2003 | Spenser et al. |
| 2003/0167089 A1 | 9/2003 | Lane |
| 2003/0181850 A1 | 9/2003 | Diamond et al. |
| 2003/0191519 A1 | 10/2003 | Lombardi et al. |
| 2003/0199913 A1 | 10/2003 | Dubrul et al. |
| 2003/0199963 A1 | 10/2003 | Tower et al. |
| 2003/0199971 A1 | 10/2003 | Tower et al. |
| 2003/0199972 A1 | 10/2003 | Zadno-Azizi et al. |
| 2003/0212410 A1 | 11/2003 | Stenzel et al. |
| 2003/0212452 A1 | 11/2003 | Zadno-Azizi et al. |
| 2003/0212454 A1 | 11/2003 | Scott et al. |
| 2003/0225445 A1 | 12/2003 | Derus et al. |
| 2004/0015232 A1 | 1/2004 | Shu et al. |
| 2004/0030381 A1 | 2/2004 | Shu |
| 2004/0034411 A1 | 2/2004 | Quijano et al. |
| 2004/0039436 A1 | 2/2004 | Spenser et al. |
| 2004/0049224 A1 | 3/2004 | Buehlmann et al. |
| 2004/0049262 A1 | 3/2004 | Obermiller et al. |
| 2004/0049266 A1 | 3/2004 | Anduiza et al. |
| 2004/0082904 A1 | 4/2004 | Houde et al. |
| 2004/0088045 A1 | 5/2004 | Cox |
| 2004/0093005 A1 | 5/2004 | Durcan |
| 2004/0093060 A1 | 5/2004 | Sequin et al. |
| 2004/0097788 A1 | 5/2004 | Mourles et al. |
| 2004/0098112 A1 | 5/2004 | DiMatteo et al. |
| 2004/0106976 A1 | 6/2004 | Bailey et al. |
| 2004/0106990 A1 | 6/2004 | Spence et al. |
| 2004/0111096 A1 | 6/2004 | Tu et al. |
| 2004/0116951 A1 | 6/2004 | Rosengart |
| 2004/0117004 A1 | 6/2004 | Osborne et al. |
| 2004/0122468 A1 | 6/2004 | Yodfat et al. |
| 2004/0122516 A1 | 6/2004 | Fogarty |
| 2004/0127979 A1 | 7/2004 | Wilson |
| 2004/0138742 A1 | 7/2004 | Myers et al. |
| 2004/0138743 A1 | 7/2004 | Myers et al. |
| 2004/0153146 A1 | 8/2004 | Lashinski et al. |
| 2004/0167573 A1 | 8/2004 | Williamson |
| 2004/0167620 A1 | 8/2004 | Ortiz |
| 2004/0186563 A1 | 9/2004 | Iobbi |
| 2004/0193261 A1 | 9/2004 | Berreklouw |
| 2004/0210240 A1 | 10/2004 | Saint |
| 2004/0210304 A1 | 10/2004 | Seguin et al. |
| 2004/0210307 A1 | 10/2004 | Khairkhahan |
| 2004/0215333 A1 | 10/2004 | Duran |
| 2004/0215339 A1 | 10/2004 | Drasler et al. |
| 2004/0225353 A1 | 11/2004 | McGuckin, Jr. |
| 2004/0225354 A1 | 11/2004 | Allen |
| 2004/0254636 A1 | 12/2004 | Flagle et al. |
| 2004/0260394 A1 | 12/2004 | Douk et al. |
| 2004/0267357 A1 | 12/2004 | Allen et al. |
| 2005/0010246 A1 | 1/2005 | Streeter |
| 2005/0010285 A1 | 1/2005 | Lambrecht et al. |
| 2005/0010287 A1 | 1/2005 | Macoviak |
| 2005/0015112 A1 | 1/2005 | Cohn et al. |

(56) References Cited

U.S. PATENT DOCUMENTS

| | | |
|---|---|---|
| 2005/0027348 A1 | 2/2005 | Case et al. |
| 2005/0033398 A1 | 2/2005 | Seguin |
| 2005/0043790 A1 | 2/2005 | Seguin |
| 2005/0049692 A1 | 3/2005 | Numamoto |
| 2005/0049696 A1 | 3/2005 | Siess |
| 2005/0055079 A1* | 3/2005 | Duran ............... A61F 2/2412 623/1.13 |
| 2005/0055088 A1 | 3/2005 | Liddicoat et al. |
| 2005/0060029 A1 | 3/2005 | Le |
| 2005/0060030 A1 | 3/2005 | Lashinski et al. |
| 2005/0075584 A1 | 4/2005 | Cali |
| 2005/0075712 A1 | 4/2005 | Biancucci |
| 2005/0075717 A1 | 4/2005 | Nguyen |
| 2005/0075719 A1 | 4/2005 | Bergheim |
| 2005/0075724 A1 | 4/2005 | Svanidze |
| 2005/0075725 A1 | 4/2005 | Rowe |
| 2005/0075727 A1 | 4/2005 | Wheatley |
| 2005/0075730 A1 | 4/2005 | Myers |
| 2005/0075731 A1 | 4/2005 | Artof |
| 2005/0085841 A1 | 4/2005 | Eversull et al. |
| 2005/0085842 A1 | 4/2005 | Eversull et al. |
| 2005/0085843 A1 | 4/2005 | Opolski et al. |
| 2005/0085890 A1 | 4/2005 | Rasmussen et al. |
| 2005/0085900 A1 | 4/2005 | Case et al. |
| 2005/0096568 A1 | 5/2005 | Kato |
| 2005/0096692 A1 | 5/2005 | Linder et al. |
| 2005/0096724 A1 | 5/2005 | Stenzel et al. |
| 2005/0096734 A1 | 5/2005 | Majercak et al. |
| 2005/0096735 A1 | 5/2005 | Hojeibane et al. |
| 2005/0096736 A1 | 5/2005 | Osse et al. |
| 2005/0096738 A1 | 5/2005 | Cali et al. |
| 2005/0107871 A1 | 5/2005 | Realyvasquez et al. |
| 2005/0113910 A1* | 5/2005 | Paniagua ............. A61F 2/2412 623/2.14 |
| 2005/0119688 A1 | 6/2005 | Berheim |
| 2005/0131438 A1 | 6/2005 | Cohn |
| 2005/0137682 A1 | 6/2005 | Justino |
| 2005/0137686 A1 | 6/2005 | Salahieh |
| 2005/0137688 A1 | 6/2005 | Salahieh et al. |
| 2005/0137692 A1 | 6/2005 | Haug |
| 2005/0137695 A1 | 6/2005 | Salahieh |
| 2005/0137701 A1 | 6/2005 | Salahieh |
| 2005/0143809 A1 | 6/2005 | Salahieh |
| 2005/0148997 A1 | 7/2005 | Valley et al. |
| 2005/0149181 A1 | 7/2005 | Eberhardt |
| 2005/0165477 A1 | 7/2005 | Anduiza et al. |
| 2005/0187616 A1 | 8/2005 | Realyvasquez |
| 2005/0203549 A1 | 9/2005 | Realyvasquez |
| 2005/0203605 A1 | 9/2005 | Dolan |
| 2005/0203614 A1 | 9/2005 | Forster et al. |
| 2005/0203615 A1 | 9/2005 | Forster et al. |
| 2005/0203617 A1 | 9/2005 | Forster et al. |
| 2005/0203618 A1 | 9/2005 | Sharkawy |
| 2005/0222674 A1 | 10/2005 | Paine |
| 2005/0228495 A1 | 10/2005 | Macoviak |
| 2005/0234546 A1 | 10/2005 | Nugent |
| 2005/0240200 A1 | 10/2005 | Bergheim |
| 2005/0240262 A1 | 10/2005 | White |
| 2005/0240263 A1 | 10/2005 | Fogarty et al. |
| 2005/0261759 A1 | 11/2005 | Lambrecht et al. |
| 2005/0283962 A1 | 12/2005 | Boudjemline |
| 2006/0004439 A1 | 1/2006 | Spenser et al. |
| 2006/0004469 A1 | 1/2006 | Sokel |
| 2006/0009841 A1 | 1/2006 | McGuckin et al. |
| 2006/0052867 A1 | 3/2006 | Revuelta et al. |
| 2006/0058775 A1 | 3/2006 | Stevens et al. |
| 2006/0089711 A1 | 4/2006 | Dolan |
| 2006/0100685 A1 | 5/2006 | Seguin et al. |
| 2006/0116757 A1 | 6/2006 | Lashinski et al. |
| 2006/0135964 A1 | 6/2006 | Vesely |
| 2006/0142848 A1 | 6/2006 | Gabbay |
| 2006/0167474 A1 | 7/2006 | Bloom et al. |
| 2006/0178740 A1 | 8/2006 | Stacchino et al. |
| 2006/0195134 A1 | 8/2006 | Crittenden |
| 2006/0195184 A1 | 8/2006 | Lane et al. |
| 2006/0195185 A1 | 8/2006 | Lane et al. |
| 2006/0195186 A1 | 8/2006 | Drews et al. |
| 2006/0206192 A1 | 9/2006 | Tower et al. |
| 2006/0206202 A1 | 9/2006 | Bonheoffer et al. |
| 2006/0235508 A1 | 10/2006 | Lane et al. |
| 2006/0247763 A1 | 11/2006 | Slater |
| 2006/0259134 A1 | 11/2006 | Schwammenthal et al. |
| 2006/0259136 A1 | 11/2006 | Nguyen et al. |
| 2006/0259137 A1 | 11/2006 | Artof et al. |
| 2006/0265056 A1 | 11/2006 | Nguyen et al. |
| 2006/0271166 A1 | 11/2006 | Thill et al. |
| 2006/0271175 A1 | 11/2006 | Woolfson et al. |
| 2006/0276874 A1 | 12/2006 | Wilson et al. |
| 2006/0276888 A1 | 12/2006 | Lee et al. |
| 2006/0282161 A1 | 12/2006 | Huynh et al. |
| 2007/0005129 A1 | 1/2007 | Damm et al. |
| 2007/0005131 A1 | 1/2007 | Taylor |
| 2007/0010878 A1 | 1/2007 | Raffiee et al. |
| 2007/0016286 A1 | 1/2007 | Herrmann et al. |
| 2007/0027518 A1 | 2/2007 | Case et al. |
| 2007/0027533 A1 | 2/2007 | Douk |
| 2007/0043435 A1 | 2/2007 | Seguin et al. |
| 2007/0051377 A1 | 3/2007 | Douk et al. |
| 2007/0073392 A1 | 3/2007 | Heyninck-Janitz |
| 2007/0078509 A1 | 4/2007 | Lotfy et al. |
| 2007/0078510 A1* | 4/2007 | Ryan .............. A61F 2/2418 623/1.26 |
| 2007/0088431 A1 | 4/2007 | Bourang et al. |
| 2007/0093869 A1 | 4/2007 | Bloom et al. |
| 2007/0100439 A1 | 5/2007 | Cangialosi |
| 2007/0100440 A1 | 5/2007 | Figulla |
| 2007/0100449 A1 | 5/2007 | O'Neil et al. |
| 2007/0112415 A1 | 5/2007 | Bartlett |
| 2007/0162102 A1 | 7/2007 | Ryan et al. |
| 2007/0162113 A1 | 7/2007 | Sharkawy et al. |
| 2007/0185513 A1 | 8/2007 | Woolfson et al. |
| 2007/0203391 A1 | 8/2007 | Bloom et al. |
| 2007/0225681 A1 | 9/2007 | House |
| 2007/0232898 A1 | 10/2007 | Huynh et al. |
| 2007/0233228 A1 | 10/2007 | Eberhardt et al. |
| 2007/0233237 A1 | 10/2007 | Krivoruchko |
| 2007/0233238 A1 | 10/2007 | Huynh et al. |
| 2007/0238979 A1 | 10/2007 | Huynh et al. |
| 2007/0239254 A1 | 10/2007 | Marchand et al. |
| 2007/0239265 A1 | 10/2007 | Birdsall |
| 2007/0239266 A1 | 10/2007 | Birdsall |
| 2007/0239269 A1 | 10/2007 | Dolan et al. |
| 2007/0239273 A1 | 10/2007 | Allen |
| 2007/0244544 A1 | 10/2007 | Birdsall et al. |
| 2007/0244545 A1 | 10/2007 | Birdsall et al. |
| 2007/0244546 A1 | 10/2007 | Francis |
| 2007/0244553 A1 | 10/2007 | Rafiee et al. |
| 2007/0244554 A1 | 10/2007 | Rafiee et al. |
| 2007/0244555 A1 | 10/2007 | Rafiee et al. |
| 2007/0244556 A1 | 10/2007 | Rafiee et al. |
| 2007/0244557 A1 | 10/2007 | Rafiee et al. |
| 2007/0250160 A1 | 10/2007 | Rafiee |
| 2007/0255394 A1 | 11/2007 | Ryan |
| 2007/0255396 A1 | 11/2007 | Douk et al. |
| 2007/0288000 A1 | 12/2007 | Bonan |
| 2008/0004688 A1 | 1/2008 | Spenser et al. |
| 2008/0004696 A1 | 1/2008 | Vesely |
| 2008/0009940 A1 | 1/2008 | Cribier |
| 2008/0015671 A1 | 1/2008 | Bonhoeffer |
| 2008/0021552 A1 | 1/2008 | Gabbay |
| 2008/0048656 A1 | 2/2008 | Tan |
| 2008/0065011 A1 | 3/2008 | Marchand et al. |
| 2008/0065206 A1 | 3/2008 | Liddicoat |
| 2008/0071361 A1 | 3/2008 | Tuval et al. |
| 2008/0071362 A1 | 3/2008 | Tuval et al. |
| 2008/0071363 A1 | 3/2008 | Tuval et al. |
| 2008/0071366 A1 | 3/2008 | Tuval et al. |
| 2008/0071368 A1 | 3/2008 | Tuval et al. |
| 2008/0077234 A1 | 3/2008 | Styrc |
| 2008/0082165 A1 | 4/2008 | Wilson et al. |
| 2008/0082166 A1 | 4/2008 | Styrc et al. |
| 2008/0133003 A1 | 6/2008 | Seguin et al. |
| 2008/0140189 A1 | 6/2008 | Nguyen et al. |
| 2008/0147105 A1 | 6/2008 | Wilson et al. |

(56) References Cited

U.S. PATENT DOCUMENTS

| | | | |
|---|---|---|---|
| 2008/0147180 A1 | 6/2008 | Ghione et al. |
| 2008/0147181 A1 | 6/2008 | Ghione et al. |
| 2008/0147182 A1 | 6/2008 | Righini et al. |
| 2008/0154355 A1 | 6/2008 | Benichow et al. |
| 2008/0154356 A1 | 6/2008 | Obermiller et al. |
| 2008/0161910 A1 | 7/2008 | Revuelta et al. |
| 2008/0161911 A1 | 7/2008 | Revuelta et al. |
| 2008/0183273 A1 | 7/2008 | Mesana et al. |
| 2008/0188928 A1 | 8/2008 | Salahieh et al. |
| 2008/0215143 A1 | 9/2008 | Seguin et al. |
| 2008/0215144 A1 | 9/2008 | Ryan et al. |
| 2008/0228254 A1 | 9/2008 | Ryan |
| 2008/0228263 A1 | 9/2008 | Ryan |
| 2008/0234797 A1 | 9/2008 | Styrc |
| 2008/0243246 A1 | 10/2008 | Ryan et al. |
| 2008/0255651 A1 | 10/2008 | Dwork |
| 2008/0255660 A1 | 10/2008 | Guyenot et al. |
| 2008/0255661 A1 | 10/2008 | Straubinger et al. |
| 2008/0262593 A1 | 10/2008 | Ryan et al. |
| 2008/0269878 A1 | 10/2008 | Iobbi |
| 2009/0005863 A1 | 1/2009 | Goetz et al. |
| 2009/0012600 A1* | 1/2009 | Styrc ............... A61F 2/2418 623/1.24 |
| 2009/0048656 A1 | 2/2009 | Wen |
| 2009/0054976 A1 | 2/2009 | Tuval et al. |
| 2009/0069887 A1 | 3/2009 | Righini et al. |
| 2009/0069889 A1 | 3/2009 | Suri et al. |
| 2009/0082858 A1 | 3/2009 | Nugent et al. |
| 2009/0138079 A1 | 5/2009 | Tuval et al. |
| 2009/0164004 A1 | 6/2009 | Cohn |
| 2009/0171447 A1 | 7/2009 | VonSegesser et al. |
| 2009/0192585 A1 | 7/2009 | Bloom et al. |
| 2009/0192586 A1 | 7/2009 | Tabor et al. |
| 2009/0192591 A1 | 7/2009 | Ryan et al. |
| 2009/0198316 A1 | 8/2009 | Laske et al. |
| 2009/0216310 A1 | 8/2009 | Straubinger et al. |
| 2009/0216312 A1 | 8/2009 | Straubinger et al. |
| 2009/0216313 A1 | 8/2009 | Straubinger et al. |
| 2009/0222082 A1 | 9/2009 | Lock et al. |
| 2009/0234443 A1 | 9/2009 | Ottma et al. |
| 2009/0240264 A1 | 9/2009 | Tuval et al. |
| 2009/0240320 A1 | 9/2009 | Tuval |
| 2010/0011564 A1* | 1/2010 | Millwee ............ A61F 2/2415 29/527.3 |
| 2010/0023119 A1* | 1/2010 | Yeo ................. A61F 2/2415 623/2.14 |
| 2010/0023120 A1* | 1/2010 | Holecek ........... A61F 2/2412 623/2.19 |
| 2010/0094411 A1 | 4/2010 | Tuval et al. |
| 2010/0100167 A1 | 4/2010 | Bortlein et al. |
| 2010/0131054 A1 | 5/2010 | Tuval et al. |
| 2010/0137979 A1 | 6/2010 | Tuval et al. |
| 2010/0234939 A1* | 9/2010 | Jaffe ................ A61F 2/2412 623/1.24 |

FOREIGN PATENT DOCUMENTS

| | | |
|---|---|---|
| DE | 195 32 846 | 3/1997 |
| DE | 195 46 692 A1 | 6/1997 |
| DE | 195 46 692 C2 | 6/1997 |
| DE | 198 57 887 A1 | 7/2000 |
| DE | 199 07 646 | 8/2000 |
| DE | 100 48 814 | 9/2000 |
| DE | 100 49 812 | 4/2002 |
| DE | 100 49 813 | 4/2002 |
| DE | 100 49 815 | 4/2002 |
| EP | 0103546 | 3/1984 |
| EP | 0597967 | 12/1994 |
| EP | 0850607 | 7/1998 |
| EP | 1057459 A1 | 6/2000 |
| EP | 1057460 | 12/2000 |
| EP | 1088529 | 4/2001 |
| EP | 1255510 | 11/2002 |
| EP | 0937439 B1 | 9/2003 |
| EP | 1340473 | 9/2003 |
| EP | 0819013 | 6/2004 |
| EP | 1469797 | 11/2005 |
| FR | 2788217 | 12/1999 |
| FR | 2815844 | 5/2000 |
| GB | 2056023 | 3/1981 |
| GB | 2433700 | 12/2007 |
| SU | 1271508 | 11/1986 |
| WO | 91/17720 | 11/1991 |
| WO | 93/01768 | 2/1993 |
| WO | 95/16411 | 6/1995 |
| WO | 95/29640 | 11/1995 |
| WO | 98/14137 | 4/1998 |
| WO | 98/29057 | 7/1998 |
| WO | 99/33414 | 7/1999 |
| WO | 00/41652 | 7/2000 |
| WO | 00/44313 | 8/2000 |
| WO | 00/47136 | 8/2000 |
| WO | 00/47139 | 8/2000 |
| WO | 01/35870 | 5/2001 |
| WO | 01/49213 | 7/2001 |
| WO | 01/54625 | 8/2001 |
| WO | 01/62189 | 8/2001 |
| WO | 01/64137 | 9/2001 |
| WO | 01/76510 | 10/2001 |
| WO | 02/22054 | 3/2002 |
| WO | 02/36048 | 5/2002 |
| WO | 02/41789 | 5/2002 |
| WO | 02/43620 | 6/2002 |
| WO | 02/47575 | 6/2002 |
| WO | 02/49540 | 6/2002 |
| WO | 03/003943 | 1/2003 |
| WO | 03/003949 | 1/2003 |
| WO | 03/011195 | 2/2003 |
| WO | 03/030776 | 4/2003 |
| WO | 2004/019811 | 3/2004 |
| WO | 2004/019825 | 3/2004 |
| WO | 2004/023980 | 3/2004 |
| WO | 2004/041126 | 5/2004 |
| WO | 2004/058106 | 7/2004 |
| WO | 2004/089250 | 10/2004 |
| WO | 2005/004753 | 1/2005 |
| WO | 2005/027790 | 3/2005 |
| WO | 2005/046528 | 5/2005 |
| WO | 2006/004679 | 1/2006 |
| WO | 2006/026371 | 3/2006 |
| WO | 2008/047354 | 4/2008 |
| WO | 2008/100599 | 8/2008 |
| WO | 2008/138584 | 11/2008 |
| WO | 2008/150529 | 12/2008 |
| WO | 2009/002548 | 12/2008 |
| WO | 2009/029199 | 3/2009 |
| WO | 2009/042196 | 4/2009 |
| WO | 2009/045338 | 4/2009 |
| WO | 2009/061389 | 5/2009 |
| WO | 2009/091509 | 7/2009 |
| WO | 2009/111241 | 9/2009 |

* cited by examiner

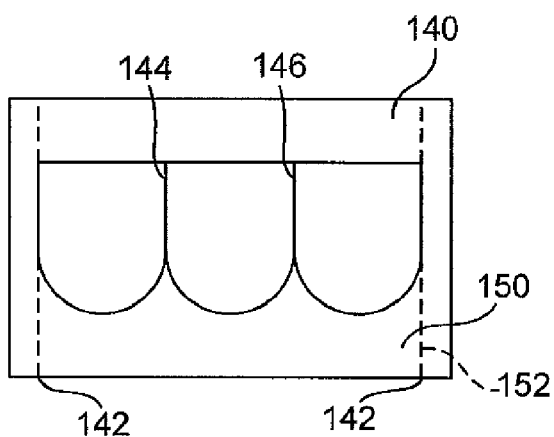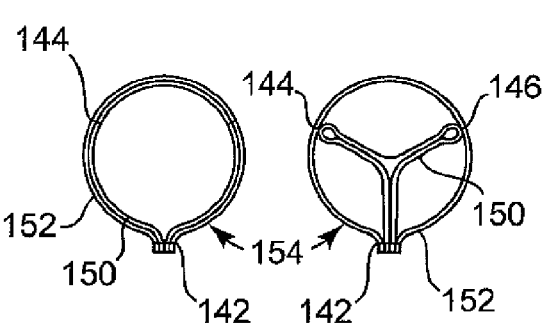
Fig. 13   Fig. 14   Fig. 15
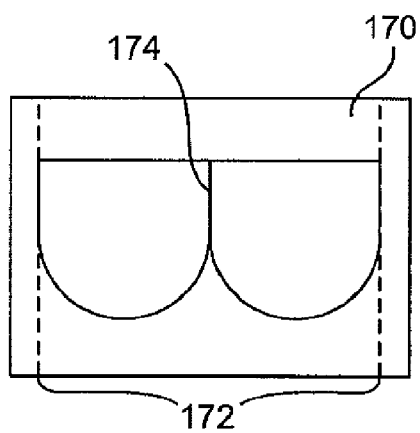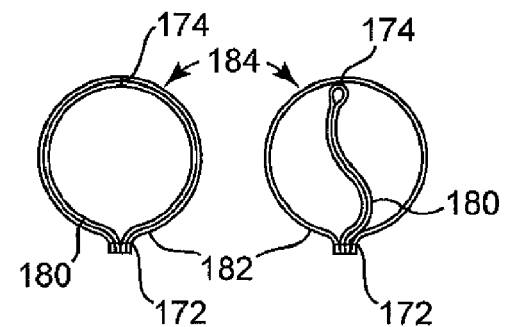
Fig. 16   Fig. 17   Fig. 18

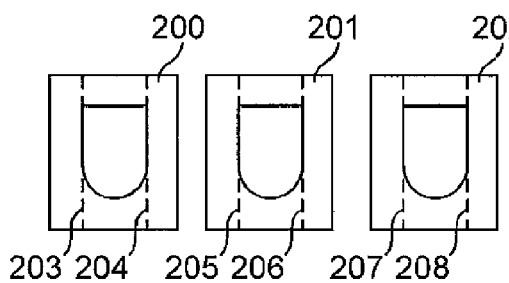
Fig. 19
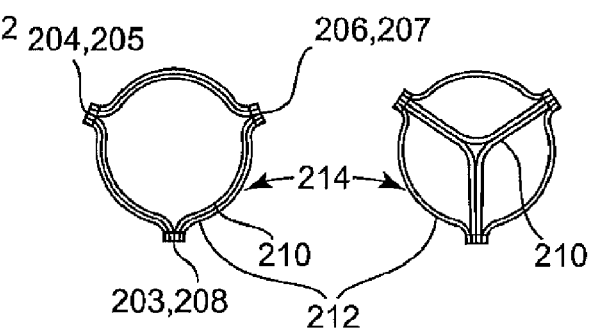
Fig. 20  Fig. 21
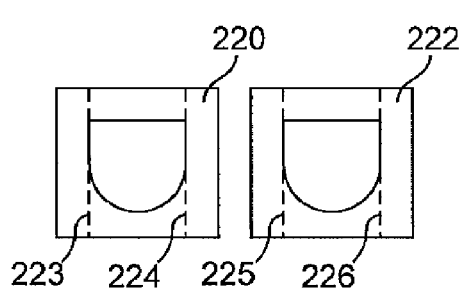
Fig. 22
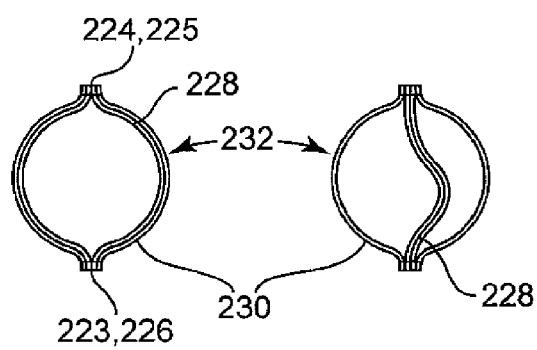
Fig. 23  Fig. 24
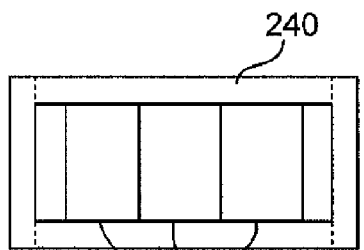
Fig. 25
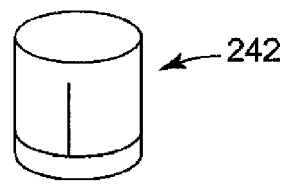
Fig. 26
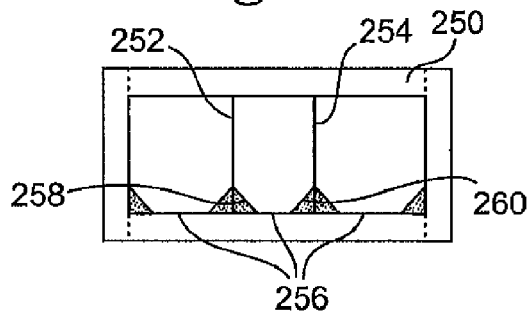
Fig. 27
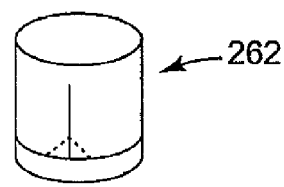
Fig. 28

PROSTHETIC CARDIAC VALVE FROM PERICARDIUM MATERIAL AND METHODS OF MAKING SAME

This application is a Continuation of co-pending application Ser. No. 11/729,680, filed Mar. 28, 2007, now U.S. Pat. No. 8,075,615, Issued Dec. 13, 2011, which claims the benefit of U.S. Provisional Application No. 60/786,849, filed on Mar. 28, 2006. The entire contents of each of these applications are hereby incorporated by reference.

PRIORITY CLAIM

This application claims the benefit of U.S. Provisional Patent Application having Ser. No. 60/786,849, filed on Mar. 28, 2006, entitled "Prosthetic Cardiac Valve Formed from Pericardium Material and Methods of Making Same", the entire disclosure of which is incorporated herein by reference for all purposes.

TECHNICAL FIELD

The present invention relates generally to treatment of cardiac heart disease. More particularly, the present invention relates to implantable valve prostheses for implantation into the cardiac system.

BACKGROUND OF THE INVENTION

The heart includes four valves that serve to direct blood flow through the two sides of the heart. On the left (systemic) side of the heart are: (1) the mitral valve, located between the left atrium and the left ventricle, and (2) the aortic valve, located between the left ventricle and the aorta. These two valves direct oxygenated blood from the lungs through the left side of the heart and into the aorta for distribution to the body. On the right (pulmonary) side of the heart are: (1) the tricuspid valve, located between the right atrium and the right ventricle, and (2) the pulmonary valve, located between the right ventricle and the pulmonary artery. These two valves direct de-oxygenated blood from the body through the right side of the heart and into the pulmonary artery for distribution to the lungs, where the blood becomes re-oxygenated in order to begin the circuit anew.

All four of these heart valves are passive structures in that they do not themselves expend any energy and do not perform any active contractile function. They consist of moveable "leaflets" that open and close in response to differential pressures on either side of the valve. Any or all of these heart valves in a particular patient may exhibit abnormal anatomy and function as a result of congenital or acquired valve disease. Congenital valve abnormalities may be well-tolerated for many years only to develop into a life-threatening problem in an elderly patient, or may be so severe that emergency surgery is required within the first few hours of life. Acquired valve disease may result from causes such as rheumatic fever, degenerative disorders of the valve tissue, bacterial or fungal infections, and trauma.

The problems that can develop with valves can generally be classified into two categories: (1) stenosis, in which a valve does not open properly, and (2) insufficiency (also called regurgitation), in which a valve does not close properly. Stenosis and insufficiency may occur concomitantly in the same valve or in different valves. Both of these abnormalities increase the workload placed on the heart. The severity of this increased stress on the heart and the patient, and the heart's ability to adapt to it, determine the treatment options that will be pursued. In some cases, medication can be sufficient to treat the patient, which is the preferred alternative; however, in many cases defective valves have to be repaired or completely replaced in order for the patient to live a normal life.

The two general categories of valves that are available for implantation into the cardiac system are mechanical valves and bioprosthetic or tissue valves. Mechanical valves have been used for many years and encompass a wide variety of designs that accommodate the blood flow requirements of the particular location where they will be implanted. Although the materials and design features of these valves are continuously being improved, they do increase the risk of clotting in the blood stream, which can lead to a heart attack or stroke. Thus, mechanical valve recipients must take anti-coagulant drugs for life to lessen the potential for blood clot formation. Further, mechanical valves can sometimes suffer from structural problems that may force the patient to have additional surgeries for further valve replacement.

Bioprosthetic valves, which are sometimes also referred to as prosthetic valves, generally include both human tissue valves and animal tissue valves. Prosthetic heart valves are described, for example, in U.S. Patent Publication No. 2004/0138742 A1 (Myers et al.), the entire contents of which are incorporated herein by reference. The designs of these bioprosthetic valves are typically relatively similar to the design of the natural valves of the patient and advantageously do not require the use of long-term anti-coagulant drugs. Human tissue valves are typically not available in large quantities since they must be removed from deceased persons who have elected organ donation; however, because large numbers of animals are routinely processed at meat processing facilities, for example, animal tissue valves are more widely available for the patients who require valve replacement. The most common types of animal tissue valves used include porcine aortic valves, and bovine and porcine pericardial valves, some of which are incorporated with some type of a stent before implantation in a patient.

To simplify surgical procedures and reduce patient trauma, there has been a recent increased interest in minimally invasive and percutaneous replacement of cardiac valves. Percutaneous replacement of a heart valve does not involve actual physical removal of the diseased or injured heart valve. Rather, the defective or injured heart valve typically remains in position while the replacement valve is inserted into a catheter and delivered percutaneously via the vascular system to the location of the failed heart valve. There, the replacement valve is either expanded by the balloon or self-expands to compress the native valve leaflets against the ventricular outflow tract, anchoring and sealing the replacement valve. In the context of percutaneous, pulmonary valve replacement, U.S. Patent Application Publication Nos. 2003/0199971 A1 (Tower, et al.) and 2003/0199963 A1 (Tower, et al.), describe a valved segment of bovine jugular vein, mounted within an expandable stent, for use as a replacement pulmonary valve. As described in the articles "Percutaneous Insertion of the Pulmonary Valve", Bonhoeffer, et al., Journal of the American College of Cardiology 2002; 39: 1664-1669 and "Transcatheter Replacement of a Bovine Valve in Pulmonary Position", Bonhoeffer, et al., Circulation 2000; 102: 813-816, the replacement pulmonary valve may be implanted to replace native pulmonary valves or prosthetic pulmonary valves located in valved conduits. Other implantables and implant delivery devices also are disclosed in published U.S. Patent Application Publication No. 2003/0036791 A1 (Bonhoeffer et al.) and European Patent Application No. 1 057 460-A1. In addition, percutaneous heart valves for use as a replacement pulmonary valve are described in Assignee's co-pending U.S.

Patent Application Publication No. 2006/0206202 A1 (Bonhoeffer et al.). Like the valves described by Tower et al., the heart valves of this co-pending application incorporate a valved segment of bovine jugular vein, which is mounted within an expandable stent.

There is, however, a continued need to be able to be able to provide a variety of different valve assemblies to accommodate the requirements of different patients, such as by providing stented valves that can be designed and customized for each individual patient.

SUMMARY

The present invention is directed to a prosthetic cardiac valve and methods of making such a valve. In one embodiment, the valves of the present invention involve the use of a piece of pericardium material, such as porcine pericardium, which is folded over on itself into a two-layer configuration. The layers are secured to each other in a predetermined pattern to create a series of arches or arcuate portions and vertical segments. This pericardium piece is formed into a tube and secured along its length, which may occur either before or after the predetermined pattern is made. The tubular segment can then be secured to a stent to create a stented valve, with the arches and vertical segments providing the leaflets of a valve. In one embodiment, three arch segments are provided to make a three leaflet or tri-leaflet valve, while another embodiment includes a two leaflet or bi-leaflet valve. The locations between the created arches and the fold line of the pericardium can act as a barrier to undesired abrasion between the valve or frame and the leaflets and also to prevent or minimize valve leakage should any of the valve segments fail. When the valve is a stented valve, the stent structure of the configuration is compressible and expandable to facilitate percutaneous insertion into the heart of a patient.

In one aspect of the invention, a prosthetic stented heart valve is provided which comprises a compressible and expandable stent structure having first and second opposite ends, an expanded outer periphery, and a compressed outer periphery that is at least slightly smaller than the expanded outer periphery when subjected to an external radial force. The heart valve further comprises a valve segment comprising a dual-layer sheet formed into a generally tubular shape having at least one longitudinally extending seam, and a plurality of leaflets formed by attachment of an outer layer of the dual-layer sheet to an inner layer of the dual-layer sheet in a leaflet defining pattern. At least a portion of the valve segment is positioned within at least a portion of the stent structure, and the stent structure is attached to the outer layer of the valve segment at one or more of the first and second ends of the stent structure. The dual-layer sheet may be a single sheet of material folded to provide a fold line along a first edge of the sheet, wherein the material on one side of the fold line comprises the outer layer of the dual-layer sheet and the material on the opposite side of the fold line comprises the inner layer of the dual-layer sheet. The surface area on either side of the fold line may be the same or different. The dual-layer sheet may further include multiple pieces of material that are attached to each other along multiple longitudinally extending seams.

The prosthetic valve may further include at least one opening in the outer layer of the dual-layer sheet that is spaced from both the first and second ends of the stent structure. In particular, a first opening can be configured for fluid communication with a right coronary artery when the prosthetic valve is positioned in the ascending aorta of a heart and a second opening spaced circumferentially from the first opening can be configured for fluid communication with a left coronary artery.

BRIEF DESCRIPTION OF THE DRAWINGS

The present invention will be further explained with reference to the appended Figures, wherein like structure is referred to by like numerals throughout the several views, and wherein:

FIG. 13 is a top view of an embodiment of a piece of dual-layer material having another leaflet and attachment pattern, which is capable of being formed into a cardiac valve in accordance with the invention;

FIGS. 14 and 15 are end views of a tubular valve made of the piece of material of FIG. 13, where FIG. 14 shows the valve with leaflets in their open position and FIG. 15 shows the valve with leaflets in their closed position;

FIG. 16 is a top view of another embodiment of a piece of dual-layer material having another alternative leaflet and attachment pattern;

FIGS. 17 and 18 are end views of a tubular valve made of the piece of material of FIG. 16, where FIG. 17 shows the valve with leaflets in their open position and FIG. 18 shows the valve with leaflets in their closed position;

FIG. 19 is a top view of three separate dual-layer material pieces having one embodiment of a leaflet pattern;

FIGS. 20 and 21 are end views of a tubular valve made of the three pieces of material of FIG. 19, which are attached to each other in the form of a tubular valve, where FIG. 20 shows the valve with leaflets in their open position and FIG. 21 shows the valve with leaflets in their closed position;

FIG. 22 is a top view of two separate dual-layer material pieces having one embodiment of a leaflet pattern;

FIGS. 23 and 24 are end views of a tubular valve made of the two pieces of material of FIG. 22, which are attached to each other in the form of a tubular valve, where FIG. 23 shows the valve with leaflets in their open position and FIG. 24 shows the valve with leaflets in their closed position;

FIG. 25 is a top view of an embodiment of a dual-layer material having another leaflet and attachment pattern;

FIG. 26 is a perspective view of the piece of material of FIG. 25 formed into a tubular valve segment;

FIG. 27 is a top view of a dual-layer material having another leaflet and attachment pattern; and FIG. 28 is a perspective view of the piece of material of FIG. 27 formed into a tubular valve segment.

DETAILED DESCRIPTION

Figure 1:
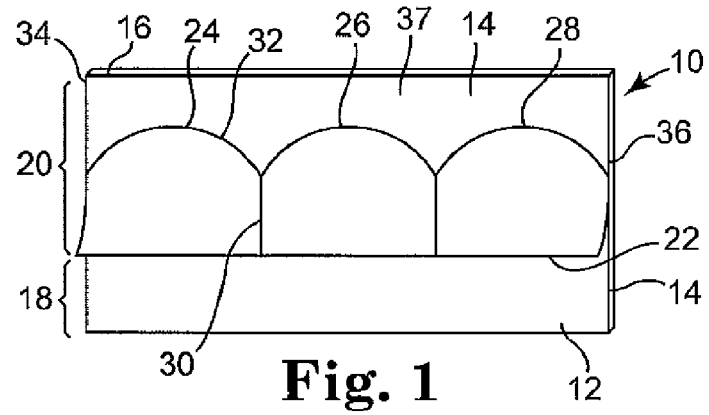
FIG. 1 is a top view of a piece of material, such as pericardium material, that is folded over onto itself to make a dual-layer configuration, in one step of being formed into a cardiac valve in accordance with the invention, including a pattern of attaching two layers of material to create a leaflet configuration.

Referring now to the Figures, wherein the components are labeled with like numerals throughout the several Figures, and initially to FIG. 1, an intermediate configuration for preparing an exemplary pericardial valve in conjunction with the methods and valves of the present invention is illustrated. The pericardial valves of the invention can be used for replacement of pulmonary valves, aortic valves, mitral valves, or tricuspid valves, in accordance with the methods of the invention described herein. Alternatively, the valves of the invention can be used to replace a failed bioprosthesis, such as in the area of an aortic valve or mitral valve, for example. The shape, size, and configuration of the outer tubular portion of the pericardial valve can specifically be designed and chosen for the type of valve that is being produced. The valves of the invention can include stented or stentless valves, but in either case, the valves are compressible to a reduced diameter during the implantation process, such as transcatheter implantation, and are capable of being expanded to a larger diameter once they are in their desired implantation location. The valve assemblies can be used as a surgical sutureless or apical implant, and can be utilized in percutaneous replacement of cardiac valves, for example. One exemplary method for assembling a stented valve of the invention generally includes the manufacture and preparation of a valve segment, then a subsequent mounting or attachment of the prepared valve segment to a stent, which is described in further detail below.

In accordance with the invention, a relatively flat sheet of pericardium material 10 is provided, which may be obtained, for example, from a porcine heart. It is understood that other donor species may alternatively be used, or that the material used is not a pericardium material but instead is a different type of tissue or material, such as a polymer or bio-engineered film. The pericardium material 10 may be at least partially fixed or cross-linked with a buffered gluteraldehyde solution or other solution at some point during the assembly process, in order to make the material easier for an operator to handle and manipulate. In one specific example, a piece of porcine pericardium is obtained, which is rinsed for approximately 10 minutes in a buffered gluteraldehyde solution to partially cross-link the material. U.S. Pat. No. 4,976,733 (Girardot), titled "Prevention of Prosthesis Calcification", describes a variety of additional exemplary methods of treating pericardium material that may be useful with the systems and methods of the present invention, along with methods for retarding or preventing the calcification of a prosthesis implanted in a mammal. However, such treatments to the material are optional and may be different depending on operator preference, the material chosen, and the like.

The piece of pericardium can then be cut to a predetermined shape and size, such as the rectangular piece of pericardium material 10 illustrated in FIG. 1. If the material 10 is thicker than desired, the thickness can be reduced using any of a number of methods for effectively removing some of the thickness of the pericardium material without sacrificing an undesirable amount of the strength of the material.

In accordance with one aspect of the invention, the pericardium material 10 includes a first surface 12 and an opposite second surface 14. The pericardium material 10 is folded on itself at fold line 16 to effectively double the thickness of at least a portion of the material 10. In this way, two portions of the first surface 12 will be in contact with each other adjacent to the fold line 16 and in any area where the material is doubled. In one exemplary embodiment of the invention, a portion of the material 10 having a length 20 has a double thickness and at least a portion of the pericardium material extends beyond the area having a double thickness, thereby leaving a portion of the material having a length 18 with a single material thickness. The portion having a double thickness may have a greater or smaller length 20 than the length 18 of the single thickness portion, or there may be essentially no portion having a single thickness (i.e., the material 10 is folded exactly in half).

As shown, the sheet of pericardium material 10 includes a free edge 22 that is spaced from the fold line 16 and corresponds with one end of the doubled portion. Thus, free edge 22 is immediately adjacent to the single thickness portion 18 and is preferably generally parallel to the fold line 16, although it is possible that the edge 22 and fold line 16 are not parallel to each other. The two portions of the pericardium material 10 in the doubled portion are then stitched, or otherwise attached to each other in an attachment pattern similar to that shown in FIG. 1. This attachment pattern includes three shaped portions 24, 26 and 28, each of which will correspond to a leaflet for a cardiac valve. In this embodiment, the pericardial valve is prepared to include three leaflets, as shown, but may optionally have more or less than three leaflets, which can be formed by varying the pattern to include more or less than three shaped portions. The three leaflet embodiment can be used in areas of the heart that typically have a three leaflet valve, such as the pulmonary valve and aortic valve, although the three leaflet embodiment can also be used as a replacement for the two leaflet mitral valve. Alternatively, a two leaflet or single leaflet embodiment of the valve of the invention is contemplated, which can be used in areas of the heart that typically have a three leaflet valve, such as the pulmonary valve, for example. Certain considerations for blood flow will determine particular parameters of the valve used, as will be explained in further detail below.

The shaped portion 26 of the attachment pattern includes two vertical components 30, which are spaced from each other by a distance that represents the desired width of a leaflet, and an arcuate portion 32 extending between the two vertical components 30. The vertical components 30 are generally linear and are preferably also generally parallel to each other. Alternatively, the vertical components 30 can be arranged to provide a funnel shape to the attachment pattern. The length of the vertical components 30 can be chosen to correspond to the desired depth of a pocket, such that a pattern including relatively long vertical components 30 will provide bigger or deeper pockets than a pattern having relatively short vertical components 30. In accordance with the invention, the length of the vertical components 30 can be particularly designed and selected to correspond with a desired depth of the pockets, which selection is not available when using a native valve, for example. In addition, the amount of material that extends above and below the valves can be particularly designed and selected to provide a valve that meets certain criteria desired by the surgeon, such as for ease of implantation or to provide a valve that has additional durability, for example.

In any case, all of the vertical components 30 within a particular pattern can have the same or nearly the same length in order to create leaflets that are identically or nearly identically shaped and sized. In that respect, all of the vertical components 30 can also be spaced at the same distance from each other, and also can be spaced at a distance from a corresponding edge (e.g., vertical or side edge 34 or 36) that will facilitate making the width of all of the shaped portions 24, 26, 28 the same for a particular piece of pericardium material 10, as will be described in further detail below. However, it is also contemplated that the vertical components 30 within a single pericardial valve configuration can have different lengths and/or can be spaced at different distances from each other in order to create a valve with leaflets that are not all identically sized and/or shaped.

Figure 5:
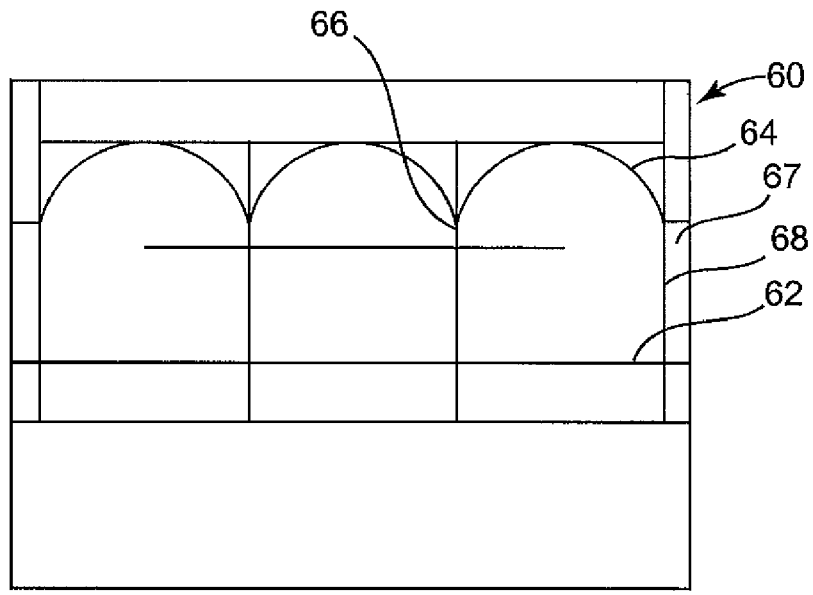
FIGS. 5 and 6 are top views of exemplary templates that can be positioned on top of the material that will be made into a cardiac valve to provide a guide for stitching patterns that can be followed in making a valve.
Figure 6:
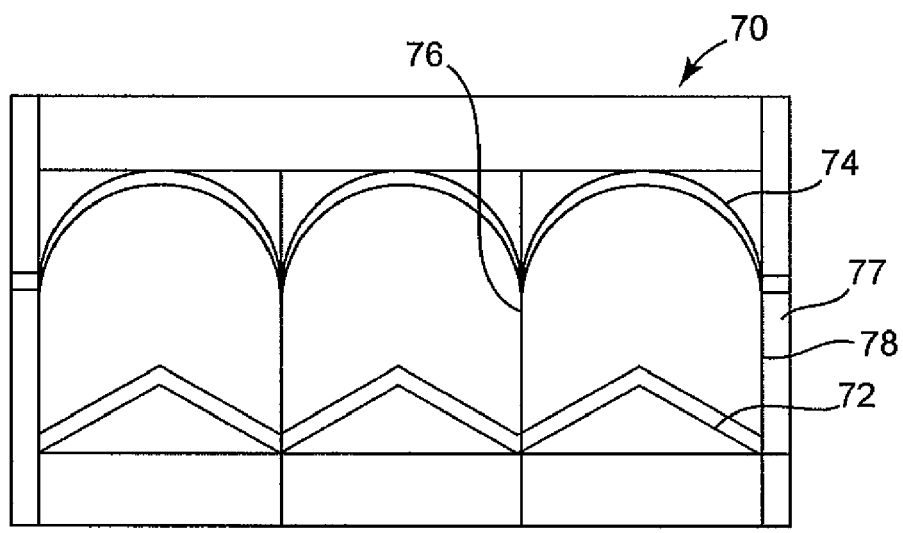

The pericardial material may be cut into the desired shape using a number of methods and apparatus, such as cutting the material with a scalpel, scissors, die, or laser. Alternatively, the attachment pattern can be determined and controlled by using a template that is positioned over the material, which may be made out of a material such as the relatively thin and translucent material commercially available under the trade name "Mylar". Two examples of such templates 60 and 70 are illustrated in FIGS. 5 and 6, respectively. The templates 60 and 70 each show a general outline that will be followed for making a valve. The tissue can be placed within a frame or other support structure to hold it in place for the securing operation, and the appropriate template can then be aligned with the tissue and tacked into place. The template 60 of FIG. 5, which includes a margin 62 that is relatively straight across the width of the template 60, illustrates one pattern that may be followed for a standard valve, while the template 70 of FIG. 6, which includes a margin 72 having portions that are angled relative to each other, illustrates one exemplary pattern that may be followed for a valve. The choice of a margin that is straight, angled, curved, or otherwise configured can be particularly selected to change the stresses that will be created on the leaflets of the valve, which depends at least partially on the particular location or position of the valve in a patient (e.g., in the area of the aortic valve or the pulmonary valve).

As shown, the pattern of template 60 includes arcuate portions 64 and vertical components 66, and the pattern of template 70 includes arcuate portions 74 and vertical components 76. The template 60 may further include tab portions 67 that extend beyond vertical stitch lines 68 on both sides of the pattern which can provide a piece of material for use in securing the material into a tube shape. That is, the tab portions provide an extending portion that can be grasped or held during the process of making the material into a tube. The template 70 includes similar tab portions 77 that extend beyond the vertical stitch lines 78 for the same purpose.

As set out above, the two thicknesses of the pericardium material 10 can be attached to each other along leaflet-defining patterns in a variety of ways, including stitching, suturing, or clamping. The suture material may be provided as a monofilament or multifilament structure made of natural or synthetic material (e.g., nylon or polypropylene), or may alternatively include an elongated metal or metal-composite thread or filament that is suitable for securing layers of pericardium material to each other. The stitching and suturing techniques will typically involve using an elongated thread-like material that may be attached to a needle to perform the securing function, which may either be done by hand or with an automated machine. Referring again to FIG. 1, such techniques would typically include pushing the needle repeatedly through both thicknesses of the pericardium material 10 in an outline shape that matches the desired pattern. Other attachment methods may also be used, including adhesives or other attachment materials that are placed in the desired attachment pattern between the two layers of the material 10, which are then pressed together to secure the first surface 12 to itself in the area between the edge 22 and the fold line 16. The attachment pattern preferably does not extend into the area 18 where the pericardium 10 is a single thickness since such stitching would serve no securing purpose. However, each of the vertical components 30 of the attachment pattern preferably has one end that terminates generally at the edge 22 of the pericardium material 10, although it is possible that the end of each vertical component 30 that is closest to the edge 22 actually terminates at a distance that is spaced at least slightly from the edge 22 toward the fold line 16.

The attachment pattern preferably extends from the edge 22 of the pericardium material 10 for a predetermined distance toward the fold line 16, but preferably does not extend all the way to the fold line 16. In this way, an area 37 of the pericardium material 10 that is between the arcuate component 32 of each of the shaped portions 24, 26, 28 and the fold line 16 includes two layers of material that are not secured to each other. For illustration purposes, the area 37 is a portion of the pericardium material 10 in FIG. 1.

Figure 2:
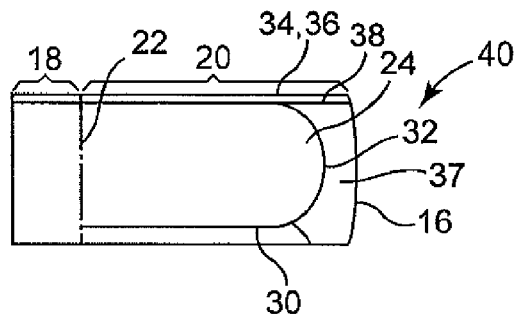
FIG. 2 is a front view of the piece of material of FIG. 1 formed into a tubular valve segment.

Referring additionally to FIG. 2, the piece of pericardium material 10 of FIG. 1, which includes the leaflet pattern described above, is then formed into a tubular shape, with the edge 22 positioned in the interior portion of the tubular shape. In order to provide the tubular configuration, the material may be formed around a mandrel or some other rigid cylindrical device. Alternatively, the material can be formed into a tubular shape without the use of a mandrel or forming device. As shown, the side edges 34, 36 of the material 10 generally meet each other at the top of the tube, with the fold line 16 illustrated at the right side of the tube. Edge 22 of material 10 is preferably positioned to be facing the interior area of the tube, which will facilitate the operation of the leaflets, as will be described below. After forming the material 10 into a tubular shape, the material 10 is secured along an attachment line 38 by stitching, suturing, or otherwise attaching the multiple thicknesses of material to each other. Attachment line 38 is preferably positioned to be as close to the edges 34, 36 as possible, although it is important that the attachment line 38 is not so close to the edges 34, 36 that there will be a risk of the stitches tearing through the material 10 or otherwise damaging the material 10. This attachment line 38 is preferably spaced at the same or a similar distance from each of the vertical components 30 as the distance between the vertical components 30 in FIG. 2. In this way, all of the shaped portions 24, 26, 28 will have a similar width, which will result in leaflets that are very similar or identical in size and shape. This tube of pericardium material 10 having leaflets that are formed by the shaped portions 24, 26, 28 may be referred to as a tubular valve segment 40.

The above description of the steps involved in making a valve segment in accordance with the invention provides the advantage of being able to perform the attachment work for the shaped portions with a flat sheet of pericardium material; however, this sequence of construction is only one exemplary way of achieving such a construction. In another alternative method, a flat sheet of pericardium material can be made into a tube by attaching opposite ends of the material to each other in a tubular shape. A portion of the pericardium material can then be folded into the inside of the tube, thereby creating an inner tube and an outer tube that is closed at the folded end and open at the opposite end. The contours or patterns for the shaped portions that will act as leaflets are then formed by stitching or otherwise attaching the two layers of material to each other, with the inflow end of the structure at the closed end of the tube and the commissures at the open end of the tube.

As described above, the area 37 between the arcuate components of the shaped portions 24, 26, 28 and the fold line 16 is an area comprising two layers of pericardium material that are not attached to each other. Once the pericardium material 10 is formed into a tube and the leaflets are formed, as described above, the area 37 is essentially an enclosed pocket area, which can serve as a backup if there are any failures in the attachment lines of the shaped portions 24, 26, and/or 28. That is, if one or more stitches or an adhesive area become unattached along some part of the shaped portions, the valve can continue to operate within the heart of a patient because the area at the fold line 16 will stop the flow of blood that might otherwise leak from the valve segment 40.

FIGS. 13 through 15 illustrate another configuration of a tri-leaflet valve having a single side seam when assembled. In particular, FIG. 13 shows a dual-layer sheet of material 140 with a scalloped pattern that is positioned between two side vertical seam lines 142 that are spaced from each other. The pattern further includes two leaflet-defining seams 144 and 146 that are spaced from each other and positioned between the vertical seam lines 142. As described above, the seam lines 142 are each preferably spaced at an equal distance from their corresponding adjacent seams 144 or 146, and seams 144 and 146 are also preferably spaced at the same distance from each other that each is positioned from the seam lines 142. However, these distances may be different, if desired. In a further alternative, the seam lines can be positioned relative to each other to provide a funnel shaped pattern. In any case, the two layers of the dual-layer sheet 140 are attached to each other generally along this pattern, such as with stitching, adhesives, or other attachment methods.

The sheet of material 140 is formed into a tubular structure having an interior layer 150 positioned closer to the central area of a valve 154, and an outer layer 152 adjacent to the interior layer 150 and positioned further from the central area of the valve 154. The two seam lines 142 are generally aligned with each other and can be connected or otherwise attached to each other using a number of attachment methods, such as sewing. The valve 154 can then be attached to a compressible stent or other compressible structure for percutaneous delivery to the heart of a patient, for example. An open position of the valve 154 is shown in FIG. 14, where the interior layer 150 has generally the same shape as the outer layer 152 (e.g, circular, as shown). A closed position of the valve 154 is shown in FIG. 15, where the interior layer 150 is scalloped or shaped to provide three leaflets.

While the stitching patterns described herein often refer to seam lines between leaflets that are generally parallel to and evenly spaced from each other, the pattern may be differently configured. For example, one or more of the seams may be angled or otherwise positioned relative to one or more adjacent seams to create relatively funnel-shaped patterns for the leaflets. These configurations may alternatively be used in embodiments of the invention that are otherwise described herein as having patterns with walls that are generally parallel to one another. It is further contemplated that a combination of parallel and non-parallel spacing of seams in a pattern can be used.

FIGS. 16 through 18 illustrate a configuration of a bi-leaflet valve having a single side seam when assembled. In particular, FIG. 16 shows a dual-layer sheet of material 170 with a scalloped pattern that is positioned between two side vertical seam lines 172 that are spaced from each other. The pattern further includes a leaflet-defining seam 174 that is positioned between the vertical seam lines 172. As described above, the seam line 172 is preferably spaced at the same distance from each of the seam lines 172. However, these distances may be different, if desired. In any case, the two layers of the dual-layer sheet 170 are attached to each other generally along this pattern, such as with stitching, adhesives, or other attachment methods.

The material 170 is formed into a tubular structure having an interior layer 180 positioned closer to the central area of a valve 184, and an outer layer 182 adjacent to the interior layer 180 and positioned further from the central area of the valve 184. The two seam lines 172 are generally aligned with each other and can be connected or otherwise attached to each other using a number of attachment methods, such as sewing. The valve 184 can then be attached to a compressible stent or other compressible structure for percutaneous delivery to the heart of a patient, for example. An open position of the valve 184 is shown in FIG. 17, where the interior layer 180 has generally the same shape as the outer layer 182 (e.g, circular, as shown). A closed position of the valve 184 is shown in FIG. 18, where the interior layer 180 is scalloped or shaped to provide two leaflets.

FIGS. 19 through 21 illustrate another configuration of a tri-leaflet valve that has three side seams instead of one when assembled. In particular, FIG. 19 includes first, second, and third pieces of dual-layer material 200, 201, 202, respectively, each of which may be a dual-layer piece of pericardium material or other material, which may be provided with two separate material pieces or by folding a piece of material along a fold line to create two material layers. First piece 200 includes vertical side seam lines 203, 204, second piece 201 includes vertical side seam lines 205, 206, and third piece 202 includes vertical side seam lines 207, 208. Each seam line of each pair of vertical side seam lines is spaced from the other seam of that pair of vertical side seam lines on its respective first, second or third material piece 200, 201, or 202. For example, side seam line 203 is spaced from side seam line 204 on first piece 200. In addition, each piece 200, 201, 202 includes a scalloped pattern for a leaflet that is positioned between its two side vertical seam lines, where each of the two vertical components of each of the scalloped patterns generally coincides with one of the vertical side seams. Each of the three pieces 200, 201, 202 can be identical in size in shape and also include identically sized and shaped patterns for the leaflets. Alternatively, the three pieces 200, 201, 202 can have somewhat different sizes, shapes, and/or patterns for the leaflets. In any case, the two layers of the dual-layer material that comprise each of the first, second, and third pieces 200, 201, 202 are attached to each other generally along their respective patterns, such as by stitching, adhesives, or other attachment methods.

The first, second, and third pieces 200, 201, 202 are formed into a tubular structure by attachment at their vertical side seam lines, such as is illustrated in FIGS. 20 and 21. In this embodiment, side seam lines of three adjacent pieces are assembled so that side seam lines 203 and 208 are generally aligned with and adjacent to each other, side seam lines 204 and 205 are generally aligned with and adjacent to each other, and side seam lines 206 and 207 are generally aligned with and adjacent to each other, thereby forming a tubular structure. Each of the pieces can be connected or otherwise attached to each other along these pairs of seam lines using a number of attachment methods, such as sewing. In this way, an interior tissue layer 210 will be positioned closer to the central area of a valve 214, and an outer layer 212 will be adjacent to the interior layer 210 and spaced further from the central area of valve 214. The valve 214 can then be attached to a compressible stent or other compressible structure for percutaneous delivery to the heart of a patient, for example. An open position of the valve 214 is shown in FIG. 20, where the interior layer 210 has generally the same shape as the outer layer 212 (e.g, circular, as shown). A closed position of the valve 214 is shown in FIG. 21, where the interior layer 210 is scalloped or shaped to provide three leaflets.

FIGS. 22 through 24 illustrate a configuration of a bi-leaflet valve having two side seams when assembled. In particular, FIG. 22 includes first and second pieces of dual-layer material 220, 222, respectively, each of which may be a piece of pericardium material. First piece 220 includes vertical side seam lines 223, 224 and second piece 222 includes vertical side seam lines 225, 226. Each piece 220, 222 includes a scalloped pattern for a leaflet that is positioned between its two side vertical seam lines, where each of the two vertical components of each of the scalloped patterns generally coincides with one of the vertical side seams. The two layers of the dual-layer material that comprise each of the first and second material pieces 220, 222 are attached to each other generally along their respective patterns, such as by stitching, adhesives, or other methods.

The first and second material pieces 220, 222, are formed into a tubular structure by attachment at their vertical side seam lines, such as is illustrated in FIGS. 23 and 24. In this embodiment, side seam lines 224 and 225 are generally aligned with and adjacent to each other, and side seam lines 223 and 226 are generally aligned with and adjacent to each other, thereby forming a tubular structure. In this way, an interior layer will be positioned closer to the central area of a valve 232, and an outer layer 230 will be positioned adjacent to the interior layer 228. The valve 232 can then be attached to a compressible stent or other compressible structure for percutaneous delivery to the heart of a patient, for example. An open position of the valve 232 is shown in FIG. 23, where the interior layer 228 has generally the same shape as the outer layer 230 (e.g, circular, as shown). A closed position of the valve 232 is shown in FIG. 24, where the interior layer 228 is scalloped or shaped to provide two leaflets.

FIG. 25 illustrates an alternative embodiment of a pattern for forming leaflets, which includes a dual-layer sheet of material 240 with layers that are attached to each other along a more rectangular pattern 244 for leaflets, as compared to the scalloped or arched shapes discussed above. The sheet of material 240 is formed into a tubular shape, such as by using the attachment and forming methods described herein, to create a valve 242 having more rectangular shaped leaflets, as shown in FIG. 26.

FIG. 27 illustrates yet another alternative embodiment of a pattern for forming leaflets, which includes a dual-layered sheet of material 250 with layers that are attached to each other to form a polygonal pattern for leaflets. One exemplary shape of the leaflets is defined by two relatively vertical components 252, 254, a relatively horizontal component 256, and two angled components 258, 260. Angled component 258 extends from component 256 to component 252, and angled component 260 extends from component 256 to component 254. The angle at which these angled components are positioned can be between at least slightly greater than approximately 0 degrees and at least slightly smaller than approximately 90 degrees. The triangular areas created by these angled components can eliminate or minimize possible areas of stasis and can also provide a non-abrasive surface over which the corresponding leaflet can hinge. The sheet of material 250 is formed into a tubular shape, such as by using the attachment and forming methods described herein, to create a valve 262 having polygonal shaped leaflets, as shown in FIG. 28.

Figure 3:
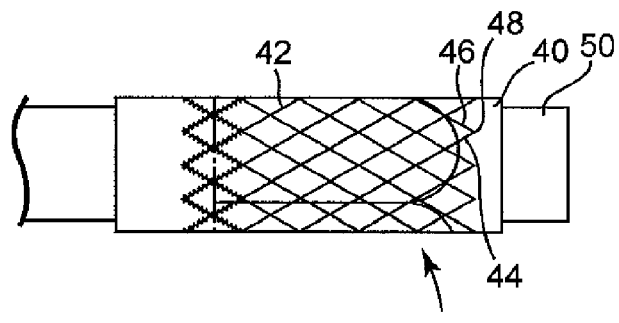
FIG. 3 is a front view of an assembly showing an exemplary initial placement of a stent over the valve segment of FIG. 2, with both the stent and valve segment positioned on a mandrel.

Referring again to FIGS. 1 and 2, the valve segment 40 described above, and any other embodiments of a valve segment of the invention, may be used alone as a stentless valve, or the valve segments may be attached to a support structure such as a stent. One exemplary configuration for mounting the valve segment 40 to a stent 42 is illustrated in FIG. 3. The stent 42, like most compressible and expandable cylindrical stents, generally takes the form of a series of zig-zag ring structures. The stent 42 illustrated corresponds generally to a stent of the type described in the above-cited Tower et al. and Bonhoeffer et al. references, for example. The stent 42 may be fabricated of platinum, stainless steel, or other biocompatible metal or polymer. Stent 42 may alternatively be fabricated using wire stock or may be produced by machining the stent from a metal tube, as is commonly employed in the manufacturing of stents. The number of wires, the positioning of such wires, and various other features of the stent chosen can vary considerably from that shown in FIG. 3. Thus, the specifics of the stent can vary widely, such that many other known generally cylindrical stent configurations may be used within the scope of the invention. The series of zig-zag ring structures of the illustrated embodiment are coupled longitudinally to one another to form a generally cylindrical-shaped structure, although it is understood that the structures can be arranged in an at least slightly oval or elliptical shape. Each ring structure takes the form of a series of adjacent generally straight sections (e.g., 44, 46), which each meet one another at one end at a curved or angled junction (e.g., junction 48) to form a "V" or "U" shaped structure.

In order to attach the tubular valve segment 40 to stent 42, the segment 40 may be partially or completely slid onto a mandrel 50, and the stent 42 can be slid over the top of the segment 40. It may be desirable to slide the tubular valve segment 40 onto the mandrel for only a portion of its length and slide the stent 42 over the segment at this point, then slide the combination of the segment 40 and the stent 42 until the remainder of the length of the segment 40 is on the mandrel. This may make it easier to keep the stent 42 positioned relative to the length of the segment 40, although it is possible to position these two components independently on the mandrel and relative to each other. It is also possible to position the valve segment relative to the stent without the use of any mandrel or other device.

Once the tubular valve segment 40 and stent 42 are positioned relative to each other so that the formed leaflets are enclosed entirely within the length of the stent 42, the stent 42 can be secured to the tubular segment 40 in a variety of ways. One procedure that can be used is to suture certain areas of the stent 42 to the tubular valve segment 40. Exemplary stitches are illustrated at one end of the stent in FIG. 3. The suture material may be provided as a monofilament or multifilament structure made of natural or synthetic materials (e.g., nylon or polypropylene), or may alternatively include an elongated metal or metal-composite thread or filament that is suitable for permanently securing the stent 42 to the tubular valve segment 40 in accordance with the present invention. The number and location of suture points can vary, but should include an adequate number of connection points that are positioned in predetermined locations that prevent movement of the stent 42 relative to the tubular valve segment 40, particularly during the compression of the stent for percutaneous delivery and expansion of the stent for its deployment. These attachment locations may include some or all of the bases of the "V's" at one or both ends of the stent 42, and may further include attachment at other areas intermediate to the ends of the stent 42. It is important, however, that the materials used for attaching the stent to the valve segment 40 do not interfere with the operation of the leaflets. That is, there should be no stitching or other attachment devices or configurations that extend through both layers of material and into the central area of any of the shaped portions 24, 26, 28, since such stitching could undesirably restrict certain movements of the leaflets, such as the efficient opening and closing of the leaflets when the valve is at the implant site of the patient.

Figure 4:
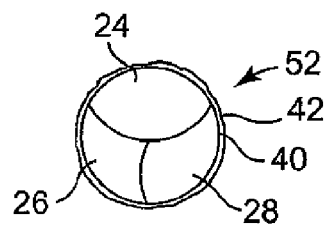
FIG. 4 is an end view of the assembly of FIG. 3 from the side of the heart into which the blood of a patient would normally flow.

Following the procedure of securing the stent 42 to the tubular valve segment 40, the stented valve can be removed from the mandrel 50. The edges of the tubular valve segment 40 extending beyond the stent 42 can optionally be trimmed to generally follow the contour of the edges of the stent 42; however, such a trimming operation may not be necessary or desirable in some applications. After removal of the valve segment 40 with attached stent 42 (referred to herein as a "stented valve 52") from the mandrel, one or more shaping tools may be temporarily inserted into the end of the stented valve 52 that is opposite the folded end 16 and into the pockets formed by the shaped portions 24, 26, 28. This procedure essentially forms a stented valve having three leaflets, where the shaping tool forces the leaflets into their closed position or configuration. FIG. 4 illustrates an end view of the valve segment 40 with attached stent 42 after removal of the shaping tool or tools, where the shaped portions 24, 26, 28 have been formed and crosslinked into leaflets that are shown in their closed positions.

Figure 7:
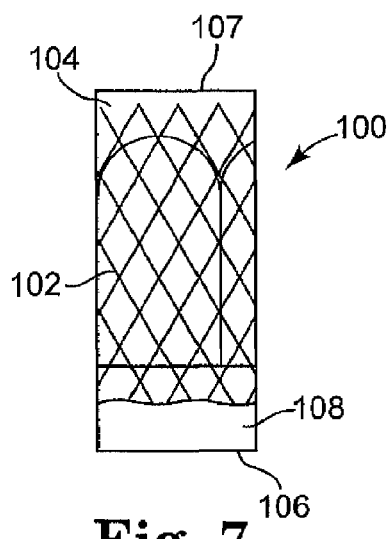
FIG. 7 is a front view of an embodiment of a cardiac valve and stent assembly of the invention.
Figure 8:
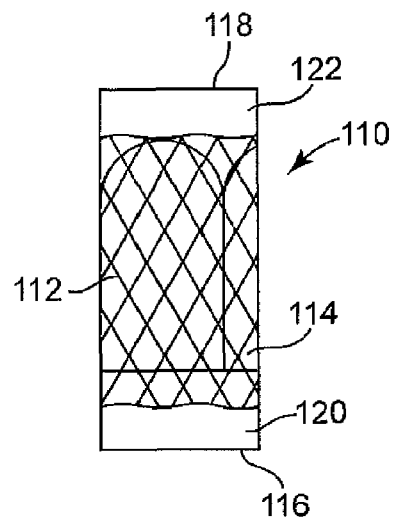
FIG. 8 is a front view of another embodiment of a cardiac valve and stent assembly of the invention.

After the tubular valve segment 40 is secured to a stent, it is contemplated that either one or both ends of the segment 40 may be rolled or folded back toward the stent, thereby increasing the thickness of the valve in these areas, as is illustrated in FIGS. 7 and 8, for two examples. In particular, FIG. 7 illustrates a stented valve 100, which includes a stent 102, a tubular valve segment 104 positioned at least partially within the stent 102, and first and second opposite ends 106, 107. Stented valve 100 further includes a portion 108 of tubular valve segment 104 that has been rolled or folded back over a portion of the stent 102 at end 106. Alternatively a portion of tubular valve segment 104 can be rolled or folded back over a portion of the stent 102 at the opposite end 107. Similarly, FIG. 8 illustrates an embodiment of a stented valve 110, which includes a stent 112, a tubular valve segment 114 positioned at least partially within the stent 112, and first and second opposite ends 116, 118. Stented valve 110 further includes rolled or folded back portions 120, 122 at opposite ends 116, 118, respectively. When both ends 116, 118 include such rolled or folded portions, the length of these portions may be the same or different from each other at opposite ends of the stented valve 110.

Figure 12:
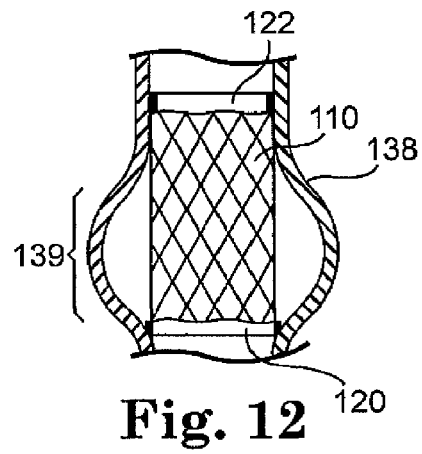
FIG. 12 is a cross-sectional side view of a cardiac valve of the invention positioned relative to a cardiac vessel.

In the embodiments described above relative to FIGS. 7 and 8, the tubular valve segments of stented valves of the invention have a ring of pericardial material that is thicker at one or both of its ends where the material is rolled or folded back on itself. This rolled-back material can overlap or cover the edge of the stent, such as to cover the edge of the stent wires, thereby making the edge or edges of the stented valve smoother. Alternatively, the material may be rolled or folded back in such a way that it does not cover the edge of the stent. For example, a folded portion of material can be positioned so that it is adjacent to an end of a stent and/or the folded portion of material can be positioned to face the interior opening or portion of the stent. In any case, the extra thickness of the material can be beneficial to prevent the stented valve from leaking around its perimeter when implanted in a patient. That is, the rolled or folded areas can help to stabilize the stented valve within the patient and can also extend into areas of the implant site that have a larger diameter as compared to the rest of the implant site. One exemplary positioning of the stented valve 110 in the ascending aorta 138 of a heart is illustrated in FIG. 12, with the portions 120, 122 that have additional thickness being positioned for sealing against the aortic walls. These rolled or folded areas can include only one additional thickness of material, such as by folding the pericardial material back once on itself, or may include multiple additional thicknesses of material, such as by folding or rolling the pericardial material back on itself multiple times. The distance that these areas protrude from the outer sides of the stent will thus depend at least partially on the number of layers of pericardial material in these areas and can therefore be provided with greater numbers of layers when a larger diameter area of the stented valve is desired.

Because the outer layer of pericardium material of the stented valve 52 (i.e., the layer that comprises the tubular valve segment 40) extends along essentially the entire length of the valve 52, as shown in FIGS. 3 and 4, for example, the leaflets are protected from contacting the wires or other materials from which the stent 42 is made when the leaflets are in an open position. In this embodiment, the leaflets will contact the outer layer of pericardium material when in their open position, thereby minimizing wear and abrasion on the leaflets. Thus, one embodiment of the invention includes maintaining the entire outer layer of pericardium material for the stented valve along the length of the valve to completely enclose and protect the leaflets of the valve. Such an embodiment of the stented valve can be used in areas where the flow of fluid moves through the ends of the valve, such as in the area of the pulmonic valve. That is, because this embodiment does not allow for fluid flow through the sides of the stented valve, this valve would not typically be used in areas that require such a flow of fluid.

Figure 9:
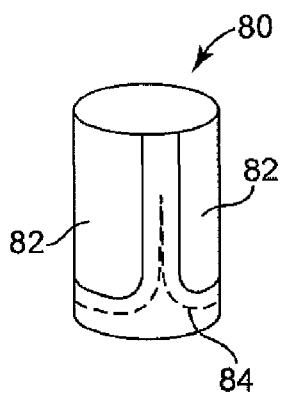
FIG. 9 is a perspective view of a valve segment of the invention with a portion of the outer tube material removed.
Figure 10:
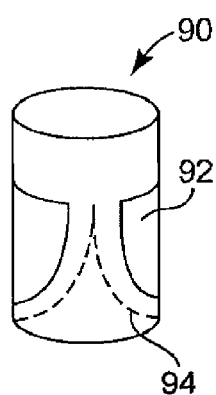
FIG. 10 is a perspective view of a valve segment of the invention with a smaller portion of the outer tube material removed as compared to the embodiment of FIG. 9, thereby leaving a top portion of the valve segment intact.
Figure 11:
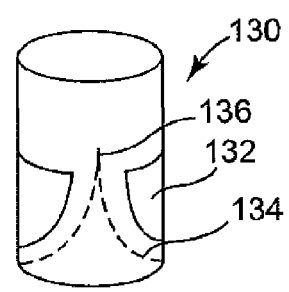
FIG. 11 is perspective view of another valve segment of the invention with a portion of the outer tube material removed to allow a particular flow of fluid through the valve.

However, FIGS. 9-11 illustrate embodiments of valves of the invention that have portions of the outer layer of material removed, which may be used with or without an outer stent. In particular, FIG. 9 illustrates a valve 80 of the invention, which includes multiple leaflets 84 that are shown in broken lines because they are positioned within the interior area of the valve 80. Sections 82 of the material of the outer tube are removed to allow for blood flow to and from the adjacent anatomy, such as the coronary arteries if the valve 80 is positioned for replacement of the aortic valve. That is, the sections 82 can be positioned for fluid communication with the sinus openings, such as in the area generally designated by reference numeral 139 in FIG. 12. The sections 82 extend generally from an area near the edge of the leaflets to the opposite edge of the valve, leaving a central support in the commissure area between the leaflets. The open sections 82 would allow for blood flow through the coronary arteries when the valve is closed.

Referring now to FIG. 10, a valve 90 of the invention is illustrated, which includes multiple leaflets 94 that are shown in broken lines. Sections 92 of the material of the outer tubular segment are removed to allow for flow to and from the adjacent anatomy, such as the coronary arteries. However, these sections 92 do not extend along as much of the length of the valve 90 as the sections 82 of the valve 80. Rather, these holes 92 are smaller and differently configured along the length of the valve 90. The valve 90 is preferably configured to allow fluid communication with certain number and spacing of anatomical vessels. For example, if the valve 90 is to be used in the area of the aortic valve, the valve preferably will include at least one opening for fluid communication with the right coronary artery and at least one opening for fluid communication with the left coronary artery. Thus, valve 90 may include only two openings 92; however, such a valve 90 would then need to be "clocked" or rotated so that one of the openings 92 lines up with the left semilunar cusp of the native valve and the other opening 92 lines up with the right semilunar cusp. In order to provide more flexibility in the positioning of valve 90, it may instead be provided with three openings 92 so that any two of the three openings 92 can be lined up with the left and right semilunar cusps and the other opening 92 can be lined up with the posterior semilunar cusp, although this opening 92 would not be in fluid communication with an artery as the other openings 92 will be.

FIG. 11 illustrates yet another valve 130 of the invention, which includes multiple leaflets 134 that are shown in broken lines. Leaflets 134 generally extend up to a point 136 at the commissures between adjacent leaflets. Sections 132 of the material of the outer tubular segment again are removed to allow for flow to and from the adjacent anatomy, such as is described above relative to FIG. 10. The openings 132 of valve 130, however, do not extend beyond the point 136. This can provide more area of the outer tubular structure against which the leaflets can open.

Preferably, when any portion of the outer layer of material of one of the valves of the invention is removed, the material is removed uniformly relative to each leaflet, in order to keep the valve structurally balanced. In addition, the amount and location of material removed from the outer layer of the valve should be designed to maintain protection of the leaflets from contact with the stent material, when a stent is used. That is, the holes made by the removal of material should be small enough and/or be oriented properly to prevent the free edge of the valve from contacting the stent through the hole in the outer layer of material. However, the material removed from the outer layer of the valve should correspond with the desired blood flow, such as being large enough and able to be aligned in the aortic position relative to the coronary blood flow.

Referring again to FIGS. 3 and 4, the stented valve 52 can be subjected to suitable chemical fixation and/or bioburden reduction treatments, which may vary considerably depending on the particular requirements for storage and use of the stented valve 52. Chemical fixation helps to preserve the tissue, render it inert, reduce the risk of host rejection, and/or the like. Chemical fixation may occur by submerging the valve in a suitable reagent for a period of about 3 hours under slight pressure and ambient temperature and then for 72 hours under ambient pressure and temperature. By way of example, a 0.2 weight percent gluteraldehyde solution at physiological pH and being phosphate buffered may be used for chemical fixation. The valve may then be stored in a suitable storage reagent (e.g., an aqueous solution containing 0.2% by weight gluteraldehyde) until subsequent use. Bioburden reduction may be carried out by submerging the tissue in a suitable reagent for a period of 48 to 72 hours at ambient temperature. By way of example, an aqueous solution containing 1% by weight gluteraldehyde and 20% by weight isopropyl alcohol at physiological pH and being phosphate-buffered may be used for bioburden reduction. This solution would be suitable for use as a packaging solution as well. A variety of fixation tines, concentrations, pH levels and chemicals can be used in accordance with the invention. After suitable treatments to the valve 52 are complete and after appropriate rinsing of the valve, the device can be used for implantation into a human.

The stented valve 52 may then be used with a system for delivering the valve segment to the desired location within a patient. The delivery system may include, for example, an outer sheath overlying an inner balloon catheter, where the outer sheath includes an expanded distal portion, within which the stented valve is located. The stented valve can be compressed around a single or double balloon located on the inner catheter. A tapered tip is mounted to the distal end of the inner catheter and serves to ease the passage of the delivery system through the patient's vasculature. The system also may include some type of guidewire to guide the delivery system to its desired implant location. Another alternative delivery system that can be used, in particular, for stented valves having a self-expanding stent, includes a catheter that does not have balloons, but instead includes a sheath or other mechanism that maintains the self-expanding stent in its compressed condition until it is desired to allow it to expand. When such a self-expanding stent is properly positioned in the patient, the mechanism that keeps the stent compressed can be retracted or otherwise removed to allow for expansion of the stent against the vessel walls.

The delivery system and its use may correspond to that described in the above-cited Tower, et al. applications, where the stented valve can be expanded against a failed native or prosthetic valve. The delivery system can be advanced to the desired valve implant site using the guidewire, after which the sheath is moved proximally, exposing the valve and balloon mounted on inner catheter. The balloon is expanded, which thereby expands stented valve 52 until it reaches a desired outer diameter where it contacts the wall of a heart vessel. The balloon is then deflated and the delivery system is withdrawn proximally.

The present invention has now been described with reference to several embodiments thereof. The entire disclosure of any patent or patent application identified herein is hereby incorporated by reference. The foregoing detailed description and examples have been given for clarity of understanding only. No unnecessary limitations are to be understood therefrom. It will be apparent to those skilled in the art that many changes can be made in the embodiments described without departing from the scope of the invention. Thus, the scope of the present invention should not be limited to the structures described herein, but only by the structures described by the language of the claims and the equivalents of those structures.

The invention claimed is:

1. A prosthetic stented heart valve comprising:
   a radially compressible and expandable tubular metal frame structure having a longitudinal axis and extending from an inflow edge along the longitudinal axis to an outflow edge along the longitudinal axis; and
   a valve segment comprising a multi-layer portion defining an inflow edge of the valve segment and a single-layer portion defining an outflow edge of the valve segment that are formed into a generally tubular shape and provide a plurality of leaflet pockets, each leaflet pocket comprising a first material layer of the multi-layer portion attached to a second material layer of the multi-layer portion with the plurality of leaflet pockets arranged together in the generally tubular shape and providing a leaflet-defining pattern that is longitudinally spaced from the inflow edge of the metal frame structure and that permits fluid flow from the inflow edge of the metal frame structure through the leaflet-defining pattern and that prevents fluid flow back through the leaflet-defining pattern toward the inflow edge of the metal frame structure, each leaflet pocket comprising an arcuate portion having a continuous arc extending from the first side edge portion to the corresponding second side edge portion, and an open edge spaced longitudinally from the arcuate portion between the first and second side edge portions, the entire arcuate portion being longitudinally spaced apart from the inflow edge of the valve segment;

wherein at least a portion of the valve segment is longitudinally positioned within the metal frame structure, and wherein the metal frame structure is attached to the first material layer of at least one leaflet pocket with the first material layer extending longitudinally at least to the inflow edge of the metal frame structure.

2. The prosthetic heart valve of claim 1, wherein the metal frame structure is attached to the first material layer at one or more of the inflow and outflow edges of the metal frame structure.

3. The prosthetic heart valve of claim 1, wherein the second material layer comprises a first end, a second end, and a seam that attaches the first end to the second end.

4. The prosthetic heart valve of claim 1, wherein each arcuate edge and the opposite side edges that extend from each arcuate edge define the leaflet-defining pattern.

5. The prosthetic heart valve of claim 1, wherein a compressed outer periphery of the metal frame structure is sized for percutaneous insertion and implantation in an anatomical structure of a patient.

6. The prosthetic heart valve of claim 1, wherein the first material layer of each leaflet pocket is a distinct piece of material from that of the other leaflet pockets.

7. The prosthetic heart valve of claim 1, wherein the second material layer of each leaflet pocket is a distinct piece of material from that of the other leaflet pockets.

8. The prosthetic heart valve of claim 7, wherein the first and second material layers are of the same material.

9. The prosthetic heart valve of claim 8, wherein the valve segment comprising a dual-layer sheet of a material that is folded along a fold line that defines the inflow edge and formed into the generally tubular shape, and the plurality of leaflet pockets are formed by attachment of an outer layer of the dual-layer sheet as the second layer to an inner layer of the dual-layer sheet as the first layer in a leaflet defining pattern.

10. A prosthetic stented heart valve comprising:
a radially compressible and expandable tubular metal frame structure having a longitudinal axis and extending from an inflow edge along the longitudinal axis to an outflow edge along the longitudinal axis; and
a valve segment comprising a multi-layer portion defining an inflow edge of the valve segment and a single-layer portion defining an outflow edge of the valve segment and providing a plurality of leaflets, the valve segment formed into a generally tubular shape, each leaflet comprising a first material layer of the multi-layer portion and a second material layer of the multi-layer portion secured to at least the first material layer with the leaflets arranged together in the generally tubular shape and providing a leaflet-defining pattern that is longitudinally spaced from the inflow edge of the metal frame structure and that permits fluid flow from the inflow edge of the metal frame structure through the leaflet-defining pattern and that prevents fluid flow back through the leaflet-defining pattern toward the inflow edge of the metal frame structure, each leaflet comprising first and second side edge portions, an arcuate portion having a continuous arc extending from the first side edge portion to the corresponding second side edge portion, and an open edge spaced from the arcuate portion, the entire arcuate portion being longitudinally spaced apart from the inflow edge of the valve segment;

wherein at least a portion of the valve segment is longitudinally positioned between the first and second edges of the metal frame structure, and wherein the metal frame structure is attached to the first material layer of at least one leaflet with the first material layer extending longitudinally to the inflow edge of the metal frame structure.

11. The prosthetic heart valve of claim 10, wherein the first material layer comprises an outer surface of the generally tubular shape of the valve segment.

12. The prosthetic heart valve of claim 10, wherein each leaflet comprises a pocket between the first and second material layers.

13. The prosthetic heart valve of claim 10, wherein the metal frame structure is attached to the first material layer at one or more of the inflow and outflow edges of the metal frame structure.

14. The prosthetic heart valve of claim 10, wherein the second material layer comprises a first end, a second end, and a seam that attaches the first end to the second end.

15. The prosthetic heart valve of claim 10, wherein each arcuate edge and the opposite side edges that extend from each arcuate edge define the leaflet-defining pattern.

16. The prosthetic heart valve of claim 10, wherein a compressed outer periphery of the metal frame structure is sized for percutaneous insertion and implantation in an anatomical structure of a patient.

17. The prosthetic heart valve of claim 10, wherein the first material layer of each leaflet pocket is a distinct piece of material from that of the other leaflet pockets.

18. The prosthetic heart valve of claim 10, wherein the second material layer of each leaflet pocket is a distinct piece of material from that of the other leaflet pockets.

19. The prosthetic heart valve of claim 18, wherein the first and second material layers are of the same material.

20. The prosthetic heart valve of claim 19, wherein the valve segment comprising a dual-layer sheet of a material that is folded along a fold line that defines the inflow edge and formed into the generally tubular shape, and the plurality of leaflet pockets are formed by attachment of an outer layer of the dual-layer sheet as the second layer to an inner layer of the dual-layer sheet as the first layer in a leaflet defining pattern.

21. The prosthetic heart valve of claim 10, wherein the arcuate portion is longitudinally spaced from the inflow edge of the valve segment such that an apex of the arcuate portion is longitudinally spaced from the inflow edge.

* * * * *